(12) United States Patent
Suda et al.

(10) Patent No.: US 10,006,013 B2
(45) Date of Patent: Jun. 26, 2018

(54) THERMOSTABLE GLYCOSIDE HYDROLASE

(71) Applicant: HONDA MOTOR CO., LTD., Minato-ku, Tokyo (JP)

(72) Inventors: Migiwa Suda, Kisarazu (JP); Jiro Okuma, Wako (JP); Asuka Yamaguchi, Tokyo (JP); Yoshitsugu Hirose, Wako (JP); Yasuhiro Kondo, Kawagoe (JP); Masaru Sato, Kisarazu (JP); Daisuke Shibata, Kisarazu (JP)

(73) Assignee: Honda Motor Co., Ltd., Tokyo (JP)

( * ) Notice: Subject to any disclaimer, the term of this patent is extended or adjusted under 35 U.S.C. 154(b) by 72 days.

(21) Appl. No.: 15/156,759

(22) Filed: May 17, 2016

(65) Prior Publication Data

US 2016/0340663 A1    Nov. 24, 2016

(30) Foreign Application Priority Data

May 19, 2015   (JP) ................................. 2015-101769

(51) Int. Cl.
| | |
|---|---|
| *C12N 9/24* | (2006.01) |
| *C12P 19/14* | (2006.01) |
| *C12N 9/42* | (2006.01) |
| *C12P 19/02* | (2006.01) |
| *C12P 19/12* | (2006.01) |

(52) U.S. Cl.
CPC ............ *C12N 9/2437* (2013.01); *C12P 19/02* (2013.01); *C12P 19/12* (2013.01); *C12P 19/14* (2013.01); *C12Y 302/01004* (2013.01)

(58) Field of Classification Search
None
See application file for complete search history.

(56) References Cited

U.S. PATENT DOCUMENTS

| | | |
|---|---|---|
| 2003/0054539 A1 | 3/2003 | Schulein et al. |
| 2012/0135499 A1 | 5/2012 | Bower et al. |
| 2016/0053246 A1 | 2/2016 | Suda et al. |

FOREIGN PATENT DOCUMENTS

| | | | |
|---|---|---|---|
| WO | 9816633 A1 | 4/1998 | |
| WO | 03012109 A1 | 2/2003 | |
| WO | 2008005529 A2 | 1/2008 | |
| WO | 2014/157492 A1 | 10/2014 | |
| WO | WO-2017087982 A2 * | 5/2017 | ............... C12Q 1/68 |

OTHER PUBLICATIONS

Park et al., "A Thermophilic Ionic Liquid-Tolerant Cellulase Cocktail for the Production of Cellulosic Biofuels", PLoS ONE 7:e37010, 2012 (Year: 2012).*
Search Report Office Action dated Jul. 15, 2016 corresponding to European Patent Application 16170320.2.
Yi et al., "Molecular and Biochemical Analyses of CbCel9A/Cel48A, a Highly Secreted Multi-Modular Cellulase by Caldicellulosiruptor bescii during Growth on Crystalline Cellulose", PLOS ONE, Dec. 2013, vol. 8, Issue 12, e84172.
Zou et al., "Construction of a cellulase hyper-expression system in Trichoderma reesei by promoter and enzyme engineering", Microbial Cell Factories, 2012, vol. 11.

* cited by examiner

*Primary Examiner* — David Steadman
(74) *Attorney, Agent, or Firm* — Carrier Blackman & Associates, P.C.; Joseph P. Carrier; Fulchand P. Shende

(57) ABSTRACT

A thermostable glycoside hydrolase includes a polypeptide including the amino acid sequence represented by SEQ ID NO: 1, and at least one moiety selected from the group consisting of a cellulose-binding module, a linker region, a signal peptide and a tag. A glycoside hydrolase mixture includes a hermostable glycoside hydrolase and at least one other glycoside hydrolase, in which the thermostable glycoside hydrolase is encoded by a polynucleotide including the nucleotide sequence encoding the polypeptide having the amino acid sequence of SEQ ID NO: 1 and the nucleotide sequence encoding at least one moiety selected from the group consisting of a cellulose-binding module, a linker region, a signal peptide and a tag. The thermostable glycoside hydrolase is produced by a method including generating the thermostable glycoside hydrolase in a transformant. The transformant is introduced in an expression vector.

8 Claims, 7 Drawing Sheets

FIG. 1

```
SD5AH4G-4     1  MEVLWVGFGKKESMRNQTKEGSDTGMTMAWKQRSGLIALILALVAGILPMGSLPKAAAEPHVDNPFGATAYVNPDYAALMDSSTARVS   90
S.aurantiaca  1  -------------------MCQRMTPRTRS----LSLARP-------------LCLLITLWGGI--AAAAVHVDNPFEGATAYVNPDYAALIDTSIAKTT  61

SD5AH4G-4    91  DPTLAAKMRTVKIYPTAVWLDRIAAIDGG----PGRRSLVQHDTALAQKQGNTPITAFVIYMPGRDCAALASNGELPLTQEGLQRYKT  177
S.aurantiaca 62  DSTLAAKMRTVKKYPTAVWLDRIAAIHGGSVNGGRKSLRDHLDLVLAQKPGQPITATFVIYDMPGRDCAALASNGELPLTPAGLQRYKA  151

SD5AH4G-4   178  EYIDRTAAHFADPNVAGIRIMIVIEPDGLPNLVTNLSDPECAQANSSGTIYYEAVRYAINKLSEIPNVVIYLDIAHSGWLGWDNNRTGAVQ  267
S.aurantiaca 152 EYIDATAAVMLADPVVQDIRIHITVIEPDGLPNLVTNLSDPECAQANSSGTIVAAARYAINKLHAIQNVYTYLDIAHSGWLGWDNNRQGIIT  241

SD5AH4G-4   268  LYINVVRGTIIGLSSVDGFVTNMANYTPLEEPYLTDPNLTVGGQPLKSAKFYEMMPYFDEMDYAAALRSAFISAGWPISIGMLIDTSRNG  357
S.aurantiaca 242 LYIDWSGTIAGLITSVDGFVTNTIANYTPLMEPNLVDPSVTVGGQQLKSAKIYEMNPLFDETDFTAALYTGFTISAGWPASIGFLIDTSRNG  331

SD5AH4G-4   358  WGGPNRPTGASGTIVDAYVDSGRVDRRAHRGLWCNMSGAGIGMPPQVAPAAYASQGIEAFVMKPPGESDGASSEIPNDEGKRFBDRMCP  447
S.aurantiaca 332 WGGPNRPTGAVGSTVDAYVDSGRVDRRAHRGLWCNOSGTIGIGQAPQSSPAGITASRLDAFVMIKPPGESDGASKEIPNEEGKGADPMCNP  421

SD5AH4G-4   448  TYTIQYGVLTGALPNAPLAGQWFHDQFVMLVQNAYPAIPTSGGGTPAPSATATPTPTPTPSVTPTPSVTPHGQLR  537
S.aurantiaca 422 DYTIKNTKAGALPMAPLSGHWFHDQFAMLVQNAYPAIPPAQ-------------------------------------  463

SD5AH4G-4   538  VVGNQLVDQNGQPIQLRGISSHGLQWYGHFVNRDSLRWLRDDWGITVFRAALYTAEQGYITNPSLKEKVKEAVQAAIELGTYVIIDMHIL  627
S.aurantiaca 463 --------------------------------------------------------------------------------  463

SD5AH4G-4   628  SDGDPNTYKEQAKAFFDEMSRLYGSYPNVIYEIANEPNGVTWEGQVKPYASEVIPVIRANDPDNLIIVGTTTWSQDVHLAADSPLPYNNL  717
S.aurantiaca 463 --------------------------------------------------------------------------------  463

SD5AH4G-4   718  AYALHFYAGTHGQWLRDRIDYARNKGIAIFVSEWGTSTSTGDGGPYLTESQQWLDFLNARQISWVNWSLSDKAESSAALLPGASATGGWT  807
S.aurantiaca 463 --------------------------------------------------------------------------------  463

SD5AH4G-4   808  DAQLSQSGRFVRAQIRSGVLTPTPAPSATPTPSVTPTVTPTSTPTPTPTPSASG  863
S.aurantiaca 463 --------------------------------------------------------------------------------  463
```

FIG. 2

| | | |
|---|---|---|
| SD5AH4G-4 | 1 | MEVLWVGFGKKESMRNQTKEGSDTGMTMAWKQRSGLIALIALVAGLLLPWGSLPKAAAEPHVDNPFVGATAVNPDYAALVDSSIARVS 90 |
| Paenibacillus sp. | 0 | ------------------------------------------------------------------------------------------ 0 |
| SD5AH4G-4 | 91 | DPTLAAKMRTVKTYPTAVWLDRIAAIDGGPRRSLVQHLDTALAQKQGNTPITAMFVIYNMPGRDCAALASNGELPLTQEGLQRYKTEYI 180 |
| Paenibacillus sp. | 0 | ------------------------------------------------------------------------------------------ 0 |
| SD5AH4G-4 | 181 | DRIAAIFADPKYAGIRIVTVIEPDGLPNLVTNLSDPECAQANSSGIYVEAVRYAINKLSEIPNVYIYLDIAHSGWLGWDNNRTGAVQLYT 270 |
| Paenibacillus sp. | 0 | ------------------------------------------------------------------------------------------ 0 |
| SD5AH4G-4 | 271 | NVVRGTTKGLSSVDGFVTNVANYTPLEEPYLTDPNLTVGGQPLKSAKFYEWNPYFDEVDYAAALRSAFISAGWPTSIGMLIDTSRNGWGG 360 |
| Paenibacillus sp. | 0 | ------------------------------------------------------------------------------------------ 0 |
| SD5AH4G-4 | 361 | PNRPTGASGTTVDAYVNSGRVDRRAHRGLWCNVSGAGIGMPPQVAPAAYASQGIEAFVWKPPGESDGASSEIPNDEGKRFDRMCDPTYT 450 |
| Paenibacillus sp. | 0 | ------------------------------------------------------------------------------------------ 0 |
| SD5AH4G-4 | 451 | TQYGVLTGALPNAPLAGQWFHDQFVMLVQNAYPAIPTSGGGTPAPSATATPTPTPTPTPTPSVTPTPSVTPTPTSSTSFVARHGQLRWG 540 |
| Paenibacillus sp. | 1 | MRIHAIRQSCRLVLTMVLMLGLLLPVGAPKGYAAPAVPFGQLKVQG 46 |
| SD5AH4G-4 | 541 | NQLVDQNGQPIQLRGISSSHGLQWYGFVANRDSLRMLRDDWGTIVFRAALYTAEQGYITNPSLKEKVKEAVQAATELGIYVIIDWHILSDG 630 |
| Paenibacillus sp. | 47 | NQLVGQSGQAVQLVGVSSHGLQWYGNFVNKSLQWVRDNWGTIVFRAAVVYTAEDGYITDPSVKVKVKEAVQASIDLGLYVIIDWHILSDG 136 |
| SD5AH4G-4 | 631 | DPNTYKEQAKAFFDEMSRIYGSYPNVIYETANEPNG-VTMEGCVKPYASEVIPVIRANDPDNLIIVGTITMSQDMHLAADSPLPYNNLAY 719 |
| Paenibacillus sp. | 137 | NPNTYKAQSKAFFQEMATLVGNTPNVIYETANEPNGVVSW-ADVKSYAEEVITAIRAIDPDGVVIVGSTMSQDIHLAADNPVSHSNMVY 225 |
| SD5AH4G-4 | 720 | ALHFYAGTHGQMLRDRIDYARNKGIAIFVSEMGTSTSTGDGGPYLTESQQMLDFLNARQISWNVWSLSDKAESSAALLPGASATGGWTDA 809 |
| Paenibacillus sp. | 226 | ALHFYSGTHGQFLRDRIITYAVMKGAAIFVTENGTSDASGNGGPYLPQSKEMDFLNARKISWNVWSLADKVETSAALMPGASPTGGWIDA 315 |
| SD5AH4G-4 | 810 | QLSQSGRFVRAQIRSGVLTPTPAPSATPTPTPSVTPTPTSPTPTPTPSG--------------------------------------- 863 |
| Paenibacillus sp. | 316 | QLSESGKWVRDQIRQATGGSGNPITAPAAPTNLSATAGNAQVSLLWNAVSGATSYTVKRATTSGGPYTNVATGVTATSYTNTGLTNGTTY 405 |
| SD5AH4G-4 | 863 | --------------------------------------------------------------------------------------- 863 |
| Paenibacillus sp. | 406 | YVVVSASNSAGSSANSAQASATPASGGASTGNLVVQYKVGDTSATDNQMKPSFNIKNNGTTPVNLSGLKLRYYFTKDGTADMSASIDWAQ 495 |
| SD5AH4G-4 | 863 | --------------------------------------------------------------------------------------- 863 |
| Paenibacillus sp. | 496 | IGASNVSAAFANFTGSNTDTYVELSFSAAAGSIPAGGQTGDIQLRMYKTDWSMFNEANDYSYDGAKTAYADMNRVTLHQNGTLVWGTTP 584 |

THERMOSTABLE GLYCOSIDE HYDROLASE

TECHNICAL FIELD

The present invention relates to a thermostable glycoside hydrolase in which a cellobiohydrolase and an endoglucanase are linked, a polynucleotide encoding the thermostable glycoside hydrolase, an expression vector for expressing the thermostable glycoside hydrolase, a transformant into which the expression vector has been incorporated, and a method for producing a cellulose degradation product using the thermostable glycoside hydrolase.

Priority is claimed on Japanese Unpublished Patent Application No. 2015-101769, filed May 19, 2015, the content of which is incorporated herein by reference.

BACKGROUND ART

Plant biomass or lignocellulose is the most plentiful renewable energy source on earth, and holds great promise as an alternative energy source to oil. The main component of plant biomass dry weight is lignocellulose, which is composed of polysaccharides such as cellulose and hemicellulose, and lignin. For example, polysaccharides can be hydrolyzed by a glycoside hydrolase such as a cellulase or hemicellulase to form monosaccharides such as glucose and xylose, which can then be used as the raw materials for biofuels or chemical products.

Lignocellulose is recalcitrant due to its complex structure, and is difficult to degrade or hydrolyze with a single glycoside hydrolase. The complete hydrolysis of lignocellulose generally requires three types of enzymes, namely an endoglucanase (cellulase or endo-1,4-β-D-glucanase, EC 3.2.1.4), an exo-type cellobiohydrolase (1,4-β-cellobiosidase or cellobiohydrolase, EC 3.2.1.91, EC 3.2.1.176), and a β-glucosidase (EC 3.2.1.21), and it is thought that the addition of a further plurality of enzymes including the hemicellulase xylanase (endo-1,4-β-xylanase, EC 3.2.1.8) and other plant cell wall-degrading enzymes such as β-xylosidase (EC 3.2.1.37) is also necessary.

In conventional bioethanol production using lignocellulose as a starting resource, hydrolysis processes using high solid loading (30 to 60% solid loading) have been tested with the aim of achieving a more energy-efficient conversion to ethanol. However, in this type of lignocellulose enzymatic hydrolysis using high solid loading, the viscosity of the hydrolyzed biomass solution is high, and the hydrolysis reaction of the lignocellulose tends to proceed poorly. Accordingly, by using a thermostable enzyme and performing the enzymatic hydrolysis process at a high temperature, for example 75° C. or higher, the rate of the hydrolysis reaction can be increased, and the viscosity of the hydrolyzed biomass solution can be reduced, which is expected to enable a shortening of the hydrolysis reaction time and a reduction in the amount of enzyme required. As a result, for all of the various glycoside hydrolases, the development of enzymes having superior thermal stability is very desirable.

Cellobiohydrolases play the most important role in the lignocellulose hydrolysis process, but the majority of these cellobiohydrolases are derived from filamentous fungi, and generally have quite poor thermostability. Only a handful of thermostable cellobiohydrolases having an optimum temperature exceeding 65° C. have been reported (for example, see Patent Document 1). A large number of thermostable endoglucanases have already been isolated from thermophilic bacteria and filamentous fungi for purposes such as lignocellulose degradation, treatment agents for cellulose fibers and paper pulp processes (for example, see Patent Document 2). In terms of thermostable cellulase multienzymes having linked catalytic domains, CelA from the thermophilic bacterium *Caldicellulosiruptor bescii* has been reported, and it has been reported that compared with the case where the catalytic domains of GH family (Glycoside Hydrolase family) 9 and GH family 48 are used individually, the cellulose degradation activity can be improved when these catalytic domains are linked (see Non-Patent Document 1).

However, there are currently no reported examples of naturally derived enzymes in which a thermostable cellobiohydrolase and a thermostable endoglucanase are linked. An enzyme prepared by artificially linking a cellobiohydrolase from the filamentous fungus *Trichoderma reesei* and an endoglucanase from the theromphilic bacterium *Acidothermus cellulolyticus* has been reported, but in addition to the linked enzyme protein, cleaved endoglucanase fragments are also produced, and the process is inefficient (see Patent Document 3, Non-Patent Document 2).

CITATION LIST

Patent Documents

Patent Document 1: International Patent Publication No. 2014/157492

Patent Document 2: U.S. Patent Application No. 2003/0054539

Patent Document 3: U.S. Patent Application No. 2012/0135499

Non-Patent Documents

Non-Patent Document 1: Yi et al., Plosone, 2013, vol. 8, e84172

Non-Patent Document 2: Zou et al., Microbial Cell Factories, 2012, vol. 11, p. 21

SUMMARY OF THE INVENTION

Problems to be Solved by the Invention

The present invention has an object of providing a polynucleotide encoding a thermostable glycoside hydrolase in which a thermostable cellobiohydrolase catalytic domain belonging to GH family 6 and a thermostable endoglucanase catalytic domain belonging to GH family 5 are linked, the thermostable glycoside hydrolase exhibiting cellobiohydrolase activity and endoglucanase activity at least at 65° C., and at least at 70° C. in the presence of calcium ions, and also has objects of providing an expression vector for expressing the thermostable glycoside hydrolase, a transformant into which the expression vector has been incorporated, and a method for producing a cellulose degradation product using the thermostable glycoside hydrolase.

Means for Solving the Problem

In order to achieve the above objects, the inventors of the present invention extracted DNA from compost cultures, and by carrying out large-scale genomic sequencing of the microbial flora that was difficult to isolate, they succeeded in obtaining a novel thermostable glycoside hydrolase in which a thermostable cellobiohydrolase catalytic domain and a thermostable endoglucanase catalytic domain were linked, thus enabling them to complete the present invention.

In other words, a thermostable glycoside hydrolase, a polynucleotide, an expression vector, a transformant, a method for producing a thermostable glycoside hydrolase, a cellulase mixture, and a method for producing a cellulose degradation product according to the present invention include the aspects [1] to [10] described below.

[1] A thermostable glycoside hydrolase, having a glycoside hydrolase catalytic domain including:

(A) a polypeptide including the amino acid sequence represented by SEQ ID NO: 1, (B) a polypeptide including an amino acid sequence in which at least one amino acid has been deleted, substituted, or added in the amino acid sequence represented by SEQ ID NO: 1, and having hydrolysis activity against a substrate of phosphoric acid swollen Avicel and hydrolysis activity against a substrate of carboxymethyl cellulose at least under conditions of 65° C. and pH 4.0, (C) a polypeptide including an amino acid sequence having 80% or greater sequence identity with the amino acid sequence represented by SEQ ID NO: 1, and having hydrolysis activity against a substrate of phosphoric acid swollen Avicel and hydrolysis activity against a substrate of carboxymethyl cellulose at least under conditions of 65° C. and pH 4.0, or (D) a polypeptide in which are linked, either directly or via a linker, a polypeptide including an amino acid sequence having 80% or greater sequence identity with the region composed of amino acids from positions 51 to 485 in the amino acid sequence represented by SEQ ID NO: 1 and having hydrolysis activity against a substrate of phosphoric acid swollen Avicel at least under conditions of 65° C. and pH 4.0, and a polypeptide including an amino acid sequence having 80% or greater sequence identity with the region composed of amino acids from positions 530 to 823 in the amino acid sequence represented by SEQ ID NO: 1 and having hydrolysis activity against a substrate of carboxymethyl cellulose at least under conditions of 65° C. and pH 4.0.

[2] The thermostable glycoside hydrolase according to [1] which, in the presence of calcium ions, exhibits hydrolysis activity against a substrate of phosphoric acid swollen Avicel and hydrolysis activity against a substrate of carboxymethyl cellulose at least under conditions of 70° C. and pH 4.0.

[3] A polynucleotide, having a region encoding a glycoside hydrolase catalytic domain, the region including:

(a) a nucleotide sequence encoding a polypeptide including the amino acid sequence represented by SEQ ID NO: 1, (b) a nucleotide sequence encoding a polypeptide which includes an amino acid sequence in which at least one amino acid has been deleted, substituted, or added in the amino acid sequence represented by SEQ ID NO: 1, and has hydrolysis activity against a substrate of phosphoric acid swollen Avicel and hydrolysis activity against a substrate of carboxymethyl cellulose at least under conditions of 65° C. and pH 4.0, (c) a nucleotide sequence encoding a polypeptide which includes an amino acid sequence having 80% or greater sequence identity with the amino acid sequence represented by SEQ ID NO: 1, and has hydrolysis activity against a substrate of phosphoric acid swollen Avicel and hydrolysis activity against a substrate of carboxymethyl cellulose at least under conditions of 65° C. and pH 4.0, (d) a nucleotide sequence encoding a polypeptide in which are linked, either directly or via a linker, a polypeptide including an amino acid sequence having 80% or greater sequence identity with the region composed of amino acids from positions 51 to 485 in the amino acid sequence represented by SEQ ID NO: 1 and having hydrolysis activity against a substrate of phosphoric acid swollen Avicel at least under conditions of 65° C. and pH 4.0, and a polypeptide including an amino acid sequence having 80% or greater sequence identity with the region composed of amino acids from positions 530 to 823 in the amino acid sequence represented by SEQ ID NO: 1 and having hydrolysis activity against a substrate of carboxymethyl cellulose at least under conditions of 65° C. and pH 4.0, (e) a nucleotide sequence having 80% or greater sequence identity with a nucleotide sequence represented by SEQ ID NO: 2, and encoding a polypeptide that has hydrolysis activity against a substrate of phosphoric acid swollen Avicel and hydrolysis activity against a substrate of carboxymethyl cellulose at least under conditions of 65° C. and pH 4.0, (f) a nucleotide sequence of a polynucleotide which hybridizes under stringent conditions with a polynucleotide including the nucleotide sequence represented by SEQ ID NO: 2, the nucleotide sequence encoding a polypeptide having hydrolysis activity against a substrate of phosphoric acid swollen Avicel and hydrolysis activity against a substrate of carboxymethyl cellulose at least under conditions of 65° C. and pH 4.0, or (g) a nucleotide sequence in which are linked, either directly or via a linker, a nucleotide sequence including a nucleotide sequence having 80% or greater sequence identity with the region composed of nucleotides from positions 153 to 1455 in the nucleotide sequence represented by SEQ ID NO: 2, and encoding a polypeptide having hydrolysis activity against a substrate of phosphoric acid swollen Avicel at least under conditions of 65° C. and pH 4.0, and a nucleotide sequence including a nucleotide sequence having 80% or greater sequence identity with the region composed of nucleotides from positions 1590 to 2469 in the nucleotide sequence represented by SEQ ID NO: 2, and encoding a polypeptide having hydrolysis activity against a substrate of carboxymethyl cellulose at least under conditions of 65° C. and pH 4.0.

[4] The polynucleotide according to [3], wherein the polypeptide also exhibits, in the presence of calcium ions, hydrolysis activity against a substrate of phosphoric acid swollen Avicel and hydrolysis activity against a substrate of carboxymethyl cellulose at least under conditions of 70° C. and pH 4.0.

[5] An expression vector incorporating the polynucleotide according to [3] or [4], the expression vector being capable of expressing, in a host cell, a polypeptide having hydrolysis activity against a substrate of phosphoric acid swollen Avicel and hydrolysis activity against a substrate of carboxymethyl cellulose.

[6] A transformant into which the expression vector according to [5] has been introduced.

[7] The transformant according to [6], which is a eukaryote.

[8] A method for producing a thermostable glycoside hydrolase, the method including generating the thermostable glycoside hydrolase in the transformant according to [6] or [7].

[9] A glycoside hydrolase mixture, including the thermostable glycoside hydrolase according to [1] or [2], a thermostable glycoside hydrolase encoded by the polynucleotide according to [3] or [4], or a thermostable glycoside hydrolase produced by the method for producing a thermostable glycoside hydrolase according to [8], and at least one other glycoside hydrolase.

[10] A method for producing a cellulose degradation product, the method including generating the cellulose degradation product by bringing a material containing cellulose into contact with the thermostable glycoside hydrolase according to [1] or [2], a thermostable glycoside hydrolase encoded by the polynucleotide according to [3] or [4], the transformant according to [6] or [7], a thermostable glycoside hydrolase produced by the method for producing a thermostable glycoside hydrolase according to [8], or the glycoside hydrolase mixture according to [9].

Effects of the Invention

The thermostable glycoside hydrolase according to the present invention has cellobiohydrolase activity and endoglucanase activity, at least at 65° C. and pH 4.0, and at least at 70° C. and pH 4.0 in the presence of calcium ions. For this reason, the thermostable glycoside hydrolase is suitable for cellulose hydrolysis processes performed under high-temperature conditions. In addition, because it has two catalytic domains within a single enzyme, use of the thermostable glycoside hydrolase according to the present invention enables a reduction in the number of enzymes required for the cellulose hydrolysis process.

Furthermore, the polynucleotide according to the present invention, an expression vector incorporating the polynucleotide, and a transformant into which the expression vector has been introduced can be used favorably in the production of the thermostable glycoside hydrolase according to the present invention.

BRIEF DESCRIPTION OF THE DRAWINGS

FIG. 1 is an alignment diagram of the amino acid sequence (SEQ ID NO: 1) encoded by an open reading frame SD5AH4G-4 and the amino acid sequence (SEQ ID NO: 6) of an exoglucanase A belonging to GH family 6 from *Stigmatella aurantiaca*.

FIG. 2 is an alignment diagram of the amino acid sequence (SEQ ID NO: 1) encoded by the open reading frame SD5AH4G-4 and the amino acid sequence (SEQ ID NO: 7) of an endoglucanase belonging to GH family 5 from *Paenibacillus* subspecies KSM-N145.

FIG. 9(B) is a diagram showing the first derivative "−d(Fluorescence)/dt" of the fluorescence intensity change curve of FIG. 9(A).

DETAILED DESCRIPTION OF THE INVENTION

[Thermostable Glycoside Hydrolase]

Figure 3:
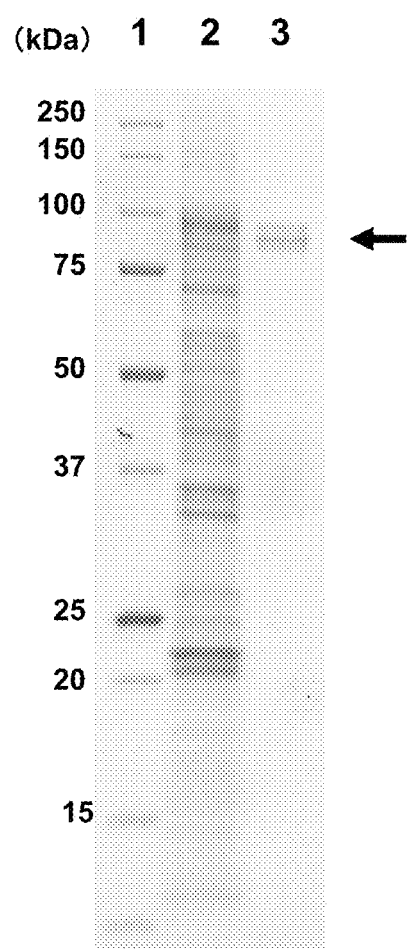
FIG. 3 is a diagram showing the SDS-PAGE analysis results of the SD5AH4G-4A-17 protein obtained by expressing the SD5AH4G-4A-17 gene in *E. coli* in Example 1.

Many microorganisms including filamentous fungi, bacteria and Archaea are difficult to culture, and it is said that about 99% of the microorganisms inhabiting microbial environments such as soil are still unknown. In particular, the culturing of microorganisms that exist in high-temperature environments is extremely difficult, and it is thought that only a mere 0.1% or less of the microorganisms that exist in natural samples collected from the natural world have been able to be isolated with currently available culturing techniques that target microorganism isolation. This difficulty in culturing microorganisms is one of the reasons hindering the development of thermostable glycoside hydrolases. Accordingly, in order to develop thermostable glycoside hydrolases, an approach that does not rely on conventional isolation and culturing techniques has been necessary.

In recent years, as a result of the development of next generation giga sequencers that enable a large amount of sequencing of giga base pairs, whole genome sequencing of the microbial flora contained in soils or the like has become possible. By using this analysis technology, the metagenomic analysis method has been proposed, in which the genomic DNA of a microbial group is prepared from an environmental sample such as soil, the genomes of the group having non-uniform and miscellaneous genomic compositions are sequenced directly and comprehensively, and the sequenced data are assembled by a parallel computer, thereby reconstructing the genomic sequences of the microbial flora. This method has contributed to rapid progress in the genome sequencing of microorganisms that are difficult to culture. However, in compost samples, where the decomposition of organic matter is proceeding vigorously, a multitude of microorganisms exist, and even if a next generation giga sequencer is used, a larger amount of sequencing is still required to comprehensively sequence the genome. Accordingly, in order to more efficiently obtain the microbial flora having the targeted properties, the inventors of the present invention used a technique in which culturing was performed in a medium that used only cellulose as a carbon source.

As shown in Example 1 described below, the inventors of the present invention extracted the genomic DNA of microbial groups from compost cultures collected from locations in Japan, and conducted shotgun sequencing and annotation of the genomic DNA, thus obtaining open reading frames (hereafter often abbreviated as ORF) encoding both amino acid sequences similar to those of known cellobiohydrolases and amino acid sequences similar to those of known endoglucanases. Primers were then designed based on the nucleotide sequence information of the obtained ORFs, and gene candidates were cloned from the genomic DNA of the compost cultures by the PCR method. The PCR-cloned DNAs were incorporated into *E. coli*, and proteins encoded by these nucleotide sequences were expressed and subjected to functional screening by phosphoric acid swollen Avicel (hereafter often abbreviated as PSA) degradation activity assay and carboxymethyl cellulose (hereafter often abbreviated as CMC) degradation activity assay. Finally, a thermostable glycoside hydrolase (hereafter also referred to as "SD5AH4G-4A-17") having both PSA degradation activity and CMC degradation activity was obtained from these ORFs. The amino acid sequence of SD5AH4G-4A-17 is represented by SEQ ID NO: 1, and the nucleotide sequence encoding the amino acid sequence of SD5AH4G-4A-17 is represented by SEQ ID NO: 2.

As shown below in Example 1 described below, SD5AH4G-4A-17 exhibits hydrolysis activity against both PSA and CMC. Further, SD5AH4G-4A-17 also exhibits degradation activity against lichenan, which is composed of glucans having β-1,3 linkages and β-1,4 linkages, and p-nitrophenyl-β-D-cellobioside (hereafter sometimes abbreviated as PNPC), and exhibits weak activity against the crystalline cellulose Avicel. This substrate specificity, and the amino acid sequence homology with known cellobiohydrolases and endoglucanases suggests that SD5AH4G-4A-17 is a multienzyme having both a cellobiohydrolase catalytic domain belonging to GH family 6 and an endoglucanase catalytic domain belonging to GH family 5.

In the present description, the expression "cellobiohydrolase activity" means activity which produces cellobiose by hydrolysis when a compound containing β-glycosidic linkages is used as the substrate.

Examples of the "compound containing β-glycosidic linkages" include glucans having β-glycosidic linkages and oligosaccharides having β-glycosidic linkages.

Further, in the present description, the expression "has activity" or "exhibits activity" means that the enzyme acts against at least one substrate, with a significant difference occurring in the amount of reducing ends or the color development reaction of the hydrolyzed substrate compared with a negative control.

Accordingly, the expression "has cellobiohydrolase activity" means that the enzyme acts at least against substrates composed of compounds containing β-glycosidic linkages, and generates a significant difference in the amount of reducing ends or the color development reaction of the hydrolyzed substrate compared with a negative control.

Further, in another aspect, the expression "has cellobiohydrolase activity" means that the enzyme acts at least against a substrate of PSA, and generates a significant difference in the amount of reducing ends or the color development reaction of the hydrolyzed substrate compared with a negative control.

Furthermore, the expression "endoglucanase activity" means activity which yields endo-hydrolysis of β-1,4-glycosidic linkages.

Accordingly, the expression "has endoglucanase activity" means that the enzyme acts at least against substrates composed of compounds containing β-1,4-glycosidic linkages, and generates a significant difference in the amount of reducing ends or the color development reaction of the hydrolyzed substrate compared with a negative control.

Further, in another aspect, the expression "has endoglucanase activity" means that the enzyme acts at least against a substrate of CMC, and generates a significant difference in the amount of reducing ends or the color development reaction of the hydrolyzed substrate compared with a negative control.

When the amino acid sequence of SD5AH4G-4A-17 was searched against a database of known amino acid sequences, sequence identity with known exoglucanases and endoglucanases suggested that within the amino acid sequence of SEQ ID NO: 1, the region composed of the amino acids from positions 51 to 485 was a cellobiohydrolase catalytic domain, and the region composed of the amino acids from positions 530 to 823 was an endoglucanase catalytic domain. The amino acid sequence that showed the highest sequence identity with the amino acid sequence of the cellobiohydrolase catalytic domain of SD5AH4G-4A-17 was a GH6 catalytic domain of an exoglucanase A (SEQ ID NO: 6) belonging to GH family 6 from the known *Stigmatella aurantiaca*, with homology (sequence identity) of 76%. Further, the amino acid sequence that showed the highest sequence identity with the amino acid sequence of the endoglucanase catalytic domain of SD5AH4G-4A-17 was a GH5 catalytic domain of an endoglucanase (SEQ ID NO: 7) belonging to GH family 5 from the known *Paenibacillus* sp. KSM-N145, with sequence identity of 73%. Moreover, because the database contained no multienzymes having both a cellobiohydrolase catalytic domain and an endoglucanase catalytic domain, no cellobiohydrolases composed of amino acid sequences that matched the cellobiohydrolase catalytic domain of SD5AH4G-4A-17, and no endoglucanases composed of amino acid sequences that matched the endoglucanase catalytic domain of SD5AH4G-4A-17, it was clear that SD5AH4G-4A-17 was a novel glycoside hydrolase.

SD5AH4G-4A-17 has cellobiohydrolase activity and endoglucanase activity at least under conditions of 65° C. and pH 4.0. Actually, as shown below in Example 1, SD5AH4G-4A-17 exhibits cellobiohydrolase activity within a broad temperature range from 20 to 85° C., and across a broad pH range from 3 to 9, and exhibits endoglucanase activity within a broad temperature range from 30 to 90° C., and across a broad pH range from 3.5 to 9.

Further, in the presence of divalent metal ions, SD5AH4G-4A-17 exhibits high cellobiohydrolase activity at even higher temperatures than those observed in the absence of such metal ions. Actually, as shown below in Example 1, in the presence of calcium ions, SD5AH4G-4A-17 has cellobiohydrolase activity at least under conditions of 70° C. and pH 4.0.

Generally, in a protein having some form of bioactivity, one or more amino acids can be deleted, substituted, or added, without impairing the bioactivity. In other words, in SD5AH4G-4A-17, one or more amino acids can be deleted, substituted, or added without impairing the cellobiohydrolase activity or the endoglucanase activity.

Hence, the thermostable glycoside hydrolase according to the present invention is a thermostable glycoside hydrolase having a glycoside hydrolase catalytic domain including any of the following (A) to (E):

(A) a polypeptide including the amino acid sequence represented by SEQ ID NO: 1, (B) a polypeptide including an amino acid sequence in which at least one amino acid has been deleted, substituted, or added in the amino acid sequence represented by SEQ ID NO: 1, and having hydrolysis activity against a substrate of PSA and hydrolysis activity against a substrate of CMC at least under conditions of 65° C. and pH 4.0, (C) a polypeptide including an amino acid sequence having 80% or greater sequence identity with the amino acid sequence represented by SEQ ID NO: 1, and having hydrolysis activity against a substrate of PSA and hydrolysis activity against a substrate of CMC at least under conditions of 65° C. and pH 4.0, (D) a polypeptide in which are linked, either directly or via a linker, a polypeptide including an amino acid sequence in which at least one amino acid has been deleted, substituted, or added in the region composed of amino acids from positions 51 to 485 in the amino acid sequence represented by SEQ ID NO: 1, and having hydrolysis activity against a substrate of PSA at least under conditions of 65° C. and pH 4.0, and a polypeptide including an amino acid sequence in which at least one amino acid has been deleted, substituted, or added in the region composed of amino acids from positions 530 to 823 in the amino acid sequence represented by SEQ ID NO: 1, and having hydrolysis activity against a substrate of CMC at least under conditions of 65° C. and pH 4.0, or (E) a polypeptide in which are linked, either directly or via a linker, a polypeptide including an amino acid sequence having 80% or greater sequence identity with the region composed of amino acids from position 51 to position 485 in the amino acid sequence represented by SEQ ID NO: 1 and having hydrolysis activity against a substrate of PSA at least under conditions of 65° C. and pH 4.0, and a polypeptide including an amino acid sequence having 80% or greater sequence identity with the region composed of amino acids from positions 530 to 823 in the amino acid sequence represented by SEQ ID NO: 1 and having hydrolysis activity against a substrate of CMC at least under conditions of 65° C. and pH 4.0.

In the above polypeptide of (B), the number of amino acids deleted, substituted, or added in the amino acid sequence represented by SEQ ID NO: 1 is preferably from 1 to 20, more preferably from 1 to 10, and still more preferably from 1 to 5. Similarly, in the above polypeptide of (D), the number of amino acids deleted, substituted, or added in the amino acid sequence of either the region composed of the amino acids from positions 51 to 485 in the amino acid sequence represented by SEQ ID NO: 1, or the region composed of the amino acids from positions 530 to 823 in the amino acid sequence represented by SEQ ID NO: 1, is preferably from 1 to 20, more preferably from 1 to 10, and still more preferably from 1 to 5.

In the above polypeptide of (C), the sequence identity with the amino acid sequence represented by SEQ ID NO: 1 is not specifically limited as long as it is 80% or greater but less than 100%, but the sequence identity is preferably 85% or greater but less than 100%, more preferably 90% or greater but less than 100%, and still more preferably 95% or greater but less than 100%. Similarly, in the above polypeptide of (E), the sequence identity with the amino acid sequence of either the region composed of the amino acids from positions 51 to 485 in the amino acid sequence represented by SEQ ID NO: 1, or the region composed of the amino acids from positions 530 to 823 in the amino acid sequence represented by SEQ ID NO: 1, is not specifically limited as long as it is 80% or greater but less than 100%, but the sequence identity is preferably 85% or greater but less than 100%, more preferably 90% or greater but less than 100%, and still more preferably 95% or greater but less than 100%.

The sequence identity (homology) between a pair of amino acid sequences is determined by juxtaposing the two amino acid sequences, while inserting gaps in some parts of the sequences to account for insertions and deletions, so as to achieve the best match between corresponding amino acids, and then calculating the proportion of matched amino acids relative to the whole amino acid sequences, excluding gaps, in the resulting alignment. The sequence identity between a pair of amino acid sequences can be determined using a variety of homology search software well known in the technical field. The sequence identity values between amino acid sequences in the present invention were obtained by calculation on the basis of alignments obtained using the publicly known homology search software BLASTP.

The aforementioned polypeptides of (B) to (E) may be artificially designed, or may be homologs of SD5AH4G-4A-17 or the like, or partial proteins thereof.

Each of the aforementioned polypeptides of (A) to (E) may be chemically synthesized based on the amino acid sequence, or may be generated by a protein expression system using the polynucleotide according to the present invention described below. Further, each of the polypeptides of (B) to (E) can also be artificially synthesized based on the polypeptide including the amino acid sequence represented by SEQ ID NO: 1, by using a gene recombination technique to introduce amino acid mutation(s).

Each of the polypeptides of (A) to (E) has cellobiohydrolase activity and endoglucanase activity at least under conditions of 65° C. and pH 4.0. As a result, a thermostable glycoside hydrolase can be obtained by having any of the polypeptides of (A) to (E) as the glycoside hydrolase catalytic domain.

The thermostable glycoside hydrolase according to the present invention acts against at least both PSA and CMC as substrates.

The thermostable glycoside hydrolase may also use other β-glucans or oligosaccharides besides PSA and CMC as substrates. Examples of these other β-glucans or oligosaccharides include crystalline celluloses such as Avicel, bacterial microcrystalline cellulose (hereafter sometimes abbreviated as BMCC) and filter paper; glucans composed of β-1,4 linkages; oligosaccharides composed of β-1,4 linkages such as cellobiose; xylan; p-nitrophenyl-β-D-galactopyranoside (hereafter sometimes abbreviated as PNPGAL); p-nitrophenyl-β-D-xylopyranoside (hereafter often abbreviated as PNPX); glucans composed of β-1,3 and β-1,4 linkages such as lichenan; glucans composed of β-1,3 and β-1,6 linkages such as laminarin; glucans composed of β-1,3 linkages; glucans composed of β-1,6 linkages; and oligosaccharides composed of β-1,6 linkages such as gentiobiose. The thermostable glycoside hydrolase according to the present invention preferably acts against Avicel and lichenan substrates in addition to PSA and CMC.

The thermostable glycoside hydrolase according to the present invention exhibits hydrolysis activity against a PSA substrate (namely, cellobiohydrolase activity) at least under conditions of pH 4.0, preferably within a temperature range from 60 to 70° C., more preferably within a temperature range from 50 to 75° C., and still more preferably within a broad temperature range from 20 to 85° C. The optimum temperature of the cellobiohydrolase activity of the thermostable glycoside hydrolase according to the present invention is preferably within a temperature range from 50 to 75° C., and more preferably within a range from 60 to 70° C.

The optimum pH of the cellobiohydrolase activity of the thermostable glycoside hydrolase according to the present invention is within a range from pH 4.0 to 5.0. The thermostable glycoside hydrolase according to the present invention preferably exhibits cellobiohydrolase activity at least within a range from pH 3.5 to 7.0, and more preferably exhibits cellobiohydrolase activity within a range from pH 3.0 to 9.0.

The thermostable glycoside hydrolase according to the present invention exhibits hydrolysis activity against a CMC substrate (namely, endoglucanase activity) at least under conditions of pH 4.0, preferably within a temperature range from 60 to 80° C., more preferably within a temperature range from 50 to 85° C., and still more preferably within a broad temperature range from 30 to 90° C. The optimum temperature of the endoglucanase activity of the thermostable glycoside hydrolase according to the present invention is preferably within a temperature range from 60 to 80° C., and more preferably within a range from 65 to 80° C.

The optimum pH of the endoglucanase activity of the thermostable glycoside hydrolase according to the present invention is within a range from pH 5.0 to 7.0. The thermostable glycoside hydrolase according to the present invention preferably exhibits endoglucanase activity at least within a range from pH 4.0 to 8.0, and more preferably exhibits endoglucanase activity within a range from pH 3.0 to 9.0.

Further, in the presence of divalent metal ions, the thermostable glycoside hydrolase according to the present invention preferably exhibits superior cellobiohydrolase activity at even higher temperatures than those observed in the absence of such metal ions, more preferably exhibits cellobiohydrolase activity at least under conditions of 70° C. and pH 4.0, and still more preferably exhibits cellobiohydrolase activity across a broad temperature range from 30 to 80° C., and across a broad pH range from pH 3.0 to 9.0.

The thermostable glycoside hydrolase according to the present invention may also have, in addition to the cellobiohydrolase activity and the endoglucanase activity, other cellulose hydrolysis activity besides the cellobiohydrolase activity and endoglucanase activity. Examples of this other cellulose hydrolysis activity include xylanase activity, β-galactosidase activity, xylosidase activity or β-glucosidase activity.

The thermostable glycoside hydrolase according to the present invention may be an enzyme composed solely of the glycoside hydrolase catalytic domain including any of the aforementioned polypeptides of (A) to (E), or may be an enzyme that also includes other domains. Examples of these other domains include other domains of conventionally known glycoside hydrolases besides the glycoside hydrolase catalytic domain. For example, the thermostable glycoside hydrolase according to the present invention also includes enzymes obtained by substituting the glycoside hydrolase catalytic domain in a publicly known glycoside hydrolase with any of the aforementioned polypeptides of (A) to (E).

When the thermostable glycoside hydrolase according to the present invention includes one or more other domains besides the glycoside hydrolase catalytic domain, the thermostable glycoside hydrolase preferably includes a cellulose-binding module (hereafter sometimes abbreviated as CBM). The cellulose-binding module may be positioned upstream (on the N-terminal side) or downstream (on the C-terminal side) of the glycoside hydrolase catalytic domain. Further, the cellulose-binding module and the glycoside hydrolase catalytic domain may be either bonded directly or bonded via a linker region of appropriate length. In the thermostable glycoside hydrolase according to the present invention, a cellulose-binding module preferably exists either upstream or downstream from the glycoside hydrolase catalytic domain with a linker region positioned therebetween, and a thermostable glycoside hydrolase in which a cellulose-binding module exists upstream of the glycoside hydrolase catalytic domain with a linker region positioned therebetween is particularly preferred.

The cellulose binding module included in the thermostable glycoside hydrolase according to the present invention is a region having the ability to bind cellulose, such as the ability to bind PSA or crystalline Avicel, and there are no particular limitations on the amino acid sequence of the module. Examples of the aforementioned cellulose-binding module include the types of cellulose-binding modules present in known proteins, and appropriately modified versions thereof. Further, in those cases where the thermostable glycoside hydrolase according to the present invention includes both the glycoside hydrolase catalytic domain and a cellulose-binding module, it is preferable that these are bonded via a linker sequence. There are no particular limitations on the amino acid sequence or the length and the like of the linker sequence.

The thermostable glycoside hydrolase according to the present invention may also have, at either the N-terminal or the C-terminal, a signal peptide capable of migration to and localization within a specific region within a cell, or a signal peptide that causes secretion from a cell. Examples of these types of signal peptides include apoplastic transport signal peptides, endoplasmic reticulum retention signal peptides, nuclear transport signal peptides, and secretory signal peptides. Specific examples of the endoplasmic reticulum retention signal peptides include signal peptides including an HDEL amino acid sequence.

Furthermore, the thermostable glycoside hydrolase according to the present invention may also have various types of tags added, for example at the N-terminal or the C-terminal, so as to facilitate easy purification in the case of generation using an expression system. Examples of tags that may be used include the types of tags widely used in the expression and purification of recombinant proteins, such as His tags, HA (hemagglutinin) tags, Myc tags and Flag tags.

In other words, one aspect of the thermostable glycoside hydrolase according to the present invention contains a glycoside hydrolase catalytic domain including any of the aforementioned polypeptides of (A) to (E); and also contains, according to need, at least one moiety selected from the group consisting of a cellulose-binding module positioned either upstream (on the N-terminal side) or downstream (on the C-terminal side) of the glycoside hydrolase catalytic domain, a linker region, a signal peptide added to either the N-terminal or the C-terminal of the thermostable glycoside hydrolase, and a tag added to either the N-terminal or the C-terminal of the thermostable glycoside hydrolase.

[Polynucleotide Encoding Thermostable Glycoside Hydrolase]

The polynucleotide according to the present invention encodes the thermostable glycoside hydrolase according to the present invention. By introducing an expression vector incorporating the polynucleotide into a host, the thermostable glycoside hydrolase can be produced by using the expression system of the host.

Specifically, the polynucleotide according to the present invention is a polynucleotide having a region encoding a glycoside hydrolase catalytic domain, the region including any of the following nucleotide sequences (a) to (h):

(a) a nucleotide sequence encoding a polypeptide including the amino acid sequence represented by SEQ ID NO: 1, (b) a nucleotide sequence encoding a polypeptide which includes an amino acid sequence in which at least one amino acid has been deleted, substituted, or added in the amino acid sequence represented by SEQ ID NO: 1, and has hydrolysis activity against a substrate of PSA and hydrolysis activity against a substrate of CMC at least under conditions of 65° C. and pH 4.0, (c) a nucleotide sequence encoding a polypeptide which includes an amino acid sequence having 80% or greater sequence identity with the amino acid sequence represented by SEQ ID NO: 1, and has hydrolysis activity against a substrate of PSA and hydrolysis activity against a substrate of CMC at least under conditions of 65° C. and pH 4.0, (d) a nucleotide sequence encoding a polypeptide in which are linked, either directly or via a linker, a polypeptide including an amino acid sequence in which at least one amino acid has been deleted, substituted, or added in the region composed of amino acids from positions 51 to 485 in the amino acid sequence represented by SEQ ID NO: 1, and having hydrolysis activity against a substrate of PSA at least under conditions of 65° C. and pH 4.0, and a polypeptide including an amino acid sequence in which at least one amino acid has been deleted, substituted, or added in the region composed of amino acids from positions 530 to 823 in the amino acid sequence represented by SEQ ID NO: 1, and having hydrolysis activity against a substrate of CMC at least under conditions of 65° C. and pH 4.0, (e) a nucleotide sequence encoding a polypeptide in which are linked, either directly or via a linker, a polypeptide including an amino acid sequence having 80% or greater sequence identity with the region composed of amino acids from positions 51 to 485 in the amino acid sequence represented by SEQ ID NO: 1 and having hydrolysis activity against a substrate of PSA at least under conditions of 65° C. and pH 4.0, and a polypeptide including an amino acid sequence having 80% or greater sequence identity with the region composed of amino acids from positions 530 to 823 in the amino acid sequence represented by SEQ ID NO: 1 and having hydrolysis activity against a substrate of CMC at least under conditions of 65° C. and pH 4.0, (f) a nucleotide sequence having 80% or greater sequence identity with a nucleotide sequence represented by SEQ ID NO: 2, and encoding a polypeptide that has hydrolysis activity against a substrate of PSA and hydrolysis activity against a substrate of CMC at least under conditions of 65° C. and pH 4.0, (g) a nucleotide sequence of a polynucleotide which hybridizes under stringent conditions with a polynucleotide including the nucleotide sequence represented by SEQ ID NO: 2, the nucleotide sequence encoding a polypeptide having hydrolysis activity against a substrate of PSA and hydrolysis activity against a substrate of CMC at least under conditions of 65° C. and pH 4.0, or (h) a nucleotide sequence in which are linked, either directly or via a linker, a nucleotide sequence including a nucleotide sequence having 80% or greater sequence identity with the region composed of nucleotides from positions 153 to 1455 in the nucleotide sequence represented by SEQ ID NO: 2, and encoding a polypeptide having hydrolysis activity against a substrate of PSA at least under conditions of 65° C. and pH 4.0, and a nucleotide sequence including a nucleotide sequence having 80% or greater sequence identity with the region composed of nucleotides from positions 1590 to 2469 in the nucleotide sequence represented by SEQ ID NO: 2, and encoding a polypeptide having hydrolysis activity against a substrate of CMC at least under conditions of 65° C. and pH 4.0.

In the present description, a "polynucleotide in which a nucleotide is deleted" means a polynucleotide in which a portion of the nucleotides which constitute the polynucleotide is missing (removed).

In the present description, a "polynucleotide in which a nucleotide is substituted" means a polynucleotide in which a nucleotide which constitutes the polynucleotide has been replaced with a different nucleotide.

In the present description, a "polynucleotide in which a nucleotide is added" means a polynucleotide in which a new nucleotide has been inserted within the polynucleotide.

In the present description, the expression "stringent conditions" can be exemplified by the method disclosed in Molecular Cloning: A Laboratory Manual, Third Edition (Sambrook et al., Cold Spring Harbor Laboratory Press). This example includes conditions in which hybridization is performed by incubation in a hybridization buffer composed of 6×SSC (composition of 20×SSC: 3 M sodium chloride, 0.3 M citric acid solution, pH 7.0), 5×Denhardt's solution (composition of 100×Denhardt's solution: 2% by mass of bovine serum albumin, 2% by mass of Ficoll, 2% by mass of polyvinylpyrrolidone), 0.5% by mass of SDS, 0.1 mg/mL of salmon sperm DNA, and 50% formamide, at a temperature of 42 to 70° C. for several hours to overnight. The washing buffer used in the washing performed after the incubation is preferably 1×SSC solution containing 0.1% by mass of SDS, and is more preferably 0.1×SSC solution containing 0.1% by mass of SDS.

In the aforementioned nucleotide sequences of (a) to (h), it is preferable to select a degenerate codon having a high frequency of usage in the host. For example, the aforementioned nucleotide sequence of (a) may be either the nucleotide sequence represented by SEQ ID NO: 2, or a nucleotide sequence obtained by modifying the nucleotide sequence represented by SEQ ID NO: 2 to codons having a higher frequency of usage in the host without changing the amino acid sequence encoded by the nucleotide sequence. This modification of codons can be achieved using a known gene sequence variation technique or artificial gene synthesis.

The polynucleotide including the nucleotide sequence represented by SEQ ID NO: 2 may be chemically synthesized based on the nucleotide sequence information, or may be obtained from the natural world using gene recombination techniques as either a full length gene that encodes SD5AH4G-4A-17 (hereafter sometimes referred to as the "SD5AH4G-4A-17 gene" or the "gene clone SD5AH4G-4A-17") or a partial region thereof including the glycoside hydrolase catalytic domain. The full length of the SD5AH4G-4A-17 gene or the partial region thereof can be obtained, for example, by collecting a sample containing microorganisms from the natural world, and conducting PCR using a genomic DNA recovered from the sample as a template, with a forward primer and a reverse primer designed by normal methods based on the nucleotide sequence represented by SEQ ID NO: 2. The cDNA synthesized by a reverse transcription reaction using mRNA recovered from the sample as a template may also be used as a template.

In the aforementioned nucleotide sequence of (f), the sequence identity with the nucleotide sequence represented by SEQ ID NO: 2 is not specifically limited as long as it is 80% or greater but less than 100%, but the sequence identity is preferably 85% or greater but less than 100%, more preferably 90% or greater but less than 100%, and still more preferably 95% or greater but less than 100%.

The sequence identity (homology) between a pair of nucleotide sequences is determined by juxtaposing the two nucleotide sequences, while inserting gaps in some parts of the sequences to account for insertions and deletions, so as to achieve the best match between corresponding nucleotides, and then calculating the proportion of matched nucleotides relative to the whole nucleotide sequences, excluding gaps, in the resulting alignment. The sequence identity between a pair of nucleotide sequences can be determined using a variety of homology search software well known in the technical field. The sequence identity values between nucleotide sequences in the present invention were obtained by calculation on the basis of alignments obtained from the publicly known homology search software BLASTN.

For example, each of the polynucleotides including an aforementioned nucleotide sequence of (b) to (h) can be artificially synthesized by deleting, substituting, or adding one or a plurality of nucleotides in a polynucleotide including the nucleotide sequence represented by SEQ ID NO: 2. Further, the nucleotide sequence of (b) to (h) may also be a full length sequence of a homologous gene of the SD5AH4G-4A-17 gene or a partial sequence thereof. The homologous gene of the SD5AH4G-4A-17 gene can be obtained by a gene recombination technique used in obtaining homologous genes of a gene for which the nucleotide sequence is already known.

The polynucleotide according to the present invention may have only the regions encoding the cellobiohydrolase catalytic domain and the endoglucanase catalytic domain, or may also have, in addition to these regions, one or more other regions encoding a cellulose-binding module, a linker sequence, various types of signal peptides, or various types of tags or the like.

In other words, one aspect of the polynucleotide according to the present invention contains a region encoding a glycoside hydrolase catalytic domain, the region including one of the aforementioned nucleotide sequences of (a) to (h), and also contains, according to need, a region encoding at least one moiety selected from the group consisting of a cellulose-binding module, a linker sequence, a signal peptide and a tag.

[Expression Vector]

The expression vector according to the present invention incorporates the aforementioned polynucleotide according to the present invention, and is capable of expressing, in a host cell, a polypeptide having cellobiohydrolase activity and endoglucanase activity at least under conditions of 65° C. and pH 4.0. In other words, the expression vector of the present invention is an expression vector into which the polynucleotide according to the present invention has been incorporated in a state capable of expressing the thermostable glycoside hydrolase according to the present invention. More specifically, an expression cassette containing, in order from the upstream side, DNA having a promoter sequence, the aforementioned polynucleotide according to the present invention, and DNA having a terminator sequence, must be incorporated into the expression vector. Incorporation of the polynucleotide into the expression vector can be achieved using known gene recombination techniques, or a commercially available expression vector preparation kit may be used.

In the present description, an "expression vector" is a vector including, in order from the upstream side, DNA having a promoter sequence, DNA having a sequence for incorporating foreign DNA, and DNA having a terminator sequence.

The aforementioned expression vector may be a vector for introduction into a prokaryotic cell such as E. coli, or a vector for introduction into a eukaryotic cell such as a yeast, a filamentous fungus, an insect cultured cell, a mammalian cultured cell, or a plant cell. Any arbitrary widely used expression vector can be selected and used in accordance with the respective host.

The expression vector according to the present invention is preferably an expression vector into which not only the aforementioned polynucleotide according to the present invention, but also a drug resistance gene or the like, has been incorporated. This facilitates the screening of cells transformed by the expression vector and non-transformed cells.

Examples of the drug resistance gene include a kanamycin resistance gene, a hygromycin resistance gene and a bialaphos resistance gene.

[Transformant]

The transformant according to the present invention is a transformant into which the expression vector according to the present invention has been introduced. In this transformant, the thermostable glycoside hydrolase according to the present invention can be expressed. Conventionally known glycoside hydrolases tend to have a narrow range of expression hosts, meaning heterologous expression is often difficult. However, the thermostable glycoside hydrolase according to the present invention can be expressed in a wide range of expression hosts, including E. coli, yeasts, filamentous fungi and higher plant chloroplasts. Accordingly, the host into which the expression vector is introduced may be a prokaryotic cell such as E. coli, or a eukaryotic cell such as a yeast, a filamentous fungus, an insect cultured cell, a mammalian cultured cell, or a plant cell. In other words, examples of the transformant according to the present invention include E. coli, a yeast, a filamentous fungus, an insect cultured cell, a mammalian cultured cell or a plant cell into which the expression vector according to the present invention has been introduced.

By culturing a transformant of E. coli, the thermostable glycoside hydrolase according to the present invention can be generated more easily and in large amounts. On the other hand, because proteins are glycosylated in eukaryotic cells, by using a transformant of a eukaryotic cell, a thermostable glycoside hydrolase can be generated which exhibits superior thermal stability to that achieved by using a transformant of a prokaryotic cell.

There are no particular limitations on the method used for producing the transformant using the expression vector, and the types of methods typically used in the production of transformants can be employed. Examples of methods that can be used include an *Agrobacterium* method, a particle gun method, an electroporation method, and a PEG (polyethylene glycol) method. Of these, if the host is a plant cell, a particle gun method or an *Agrobacterium* method is preferred.

When a prokaryotic cell, a yeast, a filamentous fungus, an insect cultured cell, or a mammalian cultured cell or the like is used as the host, the obtained transformant can generally be cultured by a conventional method in a similar manner to that of the non-transformed host.

[Method for Producing Thermostable Cellobiohydrolase]

The method for producing a thermostable glycoside hydrolase according to the present invention is a method for generating a thermostable glycoside hydrolase in the aforementioned transformant according to the present invention. By culturing a transformant that has been produced using an expression vector into which the aforementioned polynucleotide according to the present invention has been incorporated downstream from a promoter having no ability to regulate the timing or the like of the expression, the thermostable glycoside hydrolase according to the present invention can be expressed constitutively within the transformant. On the other hand, in the case of a transformant produced using a so-called expression inducible promoter to induce the expression by means of a specific compound or temperature condition or the like, the thermostable glycoside hydrolase according to the present invention can be expressed in the transformant by conducting an induction treatment suitable for the respective expression-inducing condition.

The thermostable glycoside hydrolase generated by the transformant may be used in a state where it is retained inside the transformant, or may be extracted from the transformant and purified.

The method used for extracting or purifying the thermostable glycoside hydrolase from the transformant is not particularly limited, as long as the method does not impair the cellobiohydrolase activity or the endoglucanase activity of the thermostable glycoside hydrolase, and extraction can be carried out by methods commonly used for extracting polypeptides from cells or biological tissue. Examples of the method include a method in which the transformant is immersed in an appropriate extraction buffer to extract the thermostable glycoside hydrolase, and the resulting liquid extract and the solid residue are then separated. The extraction buffer preferably contains a solubilizing agent such as a surfactant. If the transformant is a plant, then the transformant may be shredded or crushed prior to immersion in the extraction buffer. Further, in terms of the method used for separating the liquid extract and the solid residue, known solid-liquid separation treatments such as a filtration method, pressurized filtration method or centrifugation treatment may be used, or the extraction buffer containing the immersed transformant may be squeezed. The thermostable glycoside hydrolase in the liquid extract can be purified by known purification methods such as a salting-out method, ultrafiltration method, or chromatography method.

If the thermostable glycoside hydrolase according to the present invention is expressed in the transformant in a state having a secretory signal peptide, then a solution containing the thermostable glycoside hydrolase can be readily obtained by culturing the transformant and then collecting the culture liquid supernatant obtained by removal of the transformant from the obtained culture. Further, if the thermostable glycoside hydrolase according to the present invention has a tag such as a His tag, then the thermostable glycoside hydrolase in the liquid extract or in the culture supernatant can be easily purified by an affinity chromatography method using the tag.

In other words, the method for producing a thermostable glycoside hydrolase according to the present invention includes generating the thermostable glycoside hydrolase within the transformant according to the present invention, and also includes, according to need, extracting the thermostable glycoside hydrolase from the transformant and purifying the thermostable glycoside hydrolase.

[Glycoside Hydrolase Mixture]

The glycoside hydrolase mixture according to the present invention includes the aforementioned thermostable glycoside hydrolase according to the present invention or a thermostable glycoside hydrolase produced by the method for producing a thermostable glycoside hydrolase according to the present invention, and at least one other glycoside hydrolase. The thermostable glycoside hydrolase produced by the aforementioned method for producing a thermostable glycoside hydrolase according to the present invention may be in a state where it is incorporated inside the transformant, or may be extracted from the transformant and purified. By using the thermostable glycoside hydrolase according to the present invention as a mixture with one or more other glycoside hydrolases in a cellulose degradation reaction, materials composed of lignocellulose containing persistent cellulose can be degraded more efficiently.

There are no particular limitations on the other glycoside hydrolase besides the aforementioned thermostable glycoside hydrolase included in the glycoside hydrolase mixture, as long as it exhibits cellulose hydrolysis activity. Examples of the other glycoside hydrolase besides the aforementioned thermostable glycoside hydrolase included in the glycoside hydrolase mixture include hemicellulases such as xylanases and β-xylosidases, as well as cellobiohydrolases, β-glucosidases and endoglucanases. The glycoside hydrolase mixture according to the present invention is preferably a mixture containing at least one glycoside hydrolase selected from among hemicellulases and endoglucanases in addition to the aforementioned thermostable glycoside hydrolase, and is more preferably a mixture containing both a hemicellulase and an endoglucanase in addition to the aforementioned thermostable glycoside hydrolase. Among the various possibilities, the glycoside hydrolase mixture according to the present invention is preferably a mixture containing at least one glycoside hydrolase selected from the group consisting of xylanases, β-xylosidases, cellobiohydrolases and endoglucanases in addition to the aforementioned thermostable glycoside hydrolase, and is more preferably a mixture containing all of a xylanase, a β-xylosidase, a cellobiohydrolase and an endoglucanase in addition to the aforementioned thermostable glycoside hydrolase.

The other glycoside hydrolase included in the glycoside hydrolase mixture is preferably a thermostable glycoside hydrolase having glycoside hydrolase activity at least at 65° C., and is more preferably a thermostable glycoside hydrolase having glycoside hydrolase activity at 65 to 80° C. By ensuring that all of the enzymes contained in the glycoside hydrolase mixture are thermostable (that is, have an optimum temperature for the enzymatic activity or a thermal denaturation temperature for the enzyme protein of 65° C. or higher), the cellulose degradation reaction by the glycoside hydrolase mixture can be conducted efficiently under high-temperature conditions. In other words, if the glycoside hydrolase mixture contains only thermostable glycoside hydrolases, then by using the glycoside hydrolase mixture in a hydrolysis treatment of a material containing cellulose, such as a material composed of lignocellulose containing cellulose, it becomes possible to conduct a hydrolysis reaction of the material in a high-temperature environment in which the hydrolysis temperature is from 65 to 80° C. (namely, a high-temperature hydrolysis). With this high-temperature hydrolysis, the amount of enzymes and the time required for the hydrolysis can be reduced markedly, and the hydrolysis costs can be cut dramatically.

[Method for Producing Cellulose Degradation Product]

The method for producing a cellulose degradation product according to the present invention is a method for obtaining a cellulose degradation product by hydrolyzing a material containing cellulose with the thermostable glycoside hydrolase according to the present invention. More specifically, the method of the present invention is a method for producing a degradation product of a material containing cellulose (for example, a degradation product containing cellobiose and glucose and the like) by bringing the material containing cellulose into contact with the thermostable glycoside hydrolase according to the present invention, the transformant according to the present invention, a thermostable glycoside hydrolase produced using the method for producing a thermostable glycoside hydrolase according to the present invention, or the glycoside hydrolase mixture according to the present invention.

There are no particular limitations on the material containing cellulose, provided that the material contains cellulose. Specific examples of the material include cellulosic biomass such as weeds and agricultural waste materials, or used paper or the like. The material containing cellulose is preferably subjected to a mechanical treatment such as crushing or shredding, a chemical treatment with acid or alkali or the like, or a treatment such as immersion or dissolution in an appropriate buffer, prior to being brought into contact with the thermostable glycoside hydrolase according to the present invention.

The reaction conditions for the hydrolysis reaction of the above material by the thermostable glycoside hydrolase according to the present invention may be any conditions under which the thermostable glycoside hydrolase exhibits cellobiohydrolase activity and endoglucanase activity. For example, in the presence or absence of divalent metal ions, the reaction is preferably conducted at a temperature of 30 to 80° C. and a pH of 3.0 to 8.0, is more preferably conducted at a temperature of 50 to 75° C. and a pH of 3.5 to 8.0, is still more preferably conducted at a temperature of 50 to 75° C. and a pH of 4.0 to 7.0, and is most preferably conducted at a temperature of 60 to 70° C. and a pH of 4.0 to 7.0.

The reaction time for the hydrolysis reaction may be adjusted appropriately with due consideration of the type, the method of pretreatment, and the amount and the like of the material supplied to the hydrolysis reaction. For example, the hydrolysis reaction may be performed for a reaction time of 10 minutes to 100 hours, but in the case of degradation of a cellulosic biomass, the hydrolysis reaction is typically performed for a reaction time of 1 to 100 hours.

In the hydrolysis reaction of the material containing cellulose, it is also preferable to use at least one other type of glycoside hydrolase in addition to the thermostable glycoside hydrolase according to the present invention. This other glycoside hydrolase may be similar to the glycoside hydrolases mentioned above for inclusion in the aforementioned glycoside hydrolase mixture, and is preferably a thermostable glycoside hydrolase having glycoside hydrolase activity at least at 65° C., and preferably at least at temperatures of 65 to 80° C. One aspect of the aforementioned method for producing a cellulose degradation product uses the thermostable glycoside hydrolase according to the present invention, the transformant according to the present invention, or a thermostable glycoside hydrolase produced by the method for producing a thermostable glycoside hydrolase according to the present invention, whereas another aspect of the method uses the aforementioned glycoside hydrolase mixture.

EXAMPLES

Next, the present invention is described in further detail based on a series of examples, but the present invention is in no way limited by the following examples.

[Example 1] Cloning of Novel Thermostable Glycoside Hydrolase from Compost Culture Sample <1> DNA Extraction from Compost Culture Sample and Whole Genome Sequencing (WGS)

With the purpose of searching for genes of thermostable glycoside hydrolases (having an optimum temperature of 65° C. or higher), nucleotide sequencing was conducted of the genomic DNA of the microbial flora contained in compost culture samples.

Each of the compost culture samples was prepared in the following manner. First, the compost was collected. The temperature of the compost at the time of collection was within a range from 20 to 68° C. Next, about 0.5 g of the collected compost, two 1.5 cm square sheets of a thick paper (about 250 mg, gel-blotting paper GB005, manufactured by Whatman plc) as a carbon source, and one dialysis tube having dimensions of 1.2 cm×1.5 cm made of regenerated cellulose (Spectra/Por 7 RC dialysis tube, manufactured by Spectrum Laboratories, Inc.) were added to 20 mL of a modified AGS liquid medium detailed in Table 1, and a rotary shaking culture was performed at 65° C. and 120 rpm using a 125 mL conical flask fitted with baffles. After culturing for one week, and following confirmation of the disappearance of the carbon source and the proliferation of bacteria inside the conical flask, 0.5 mL of the culture medium was subcultured in a fresh 20 mL sample of the modified AGS liquid medium, and a carbon source was then added and culturing was performed in the same manner as described above.

After three repetitions of this subculturing process, the bacterial cells were collected by centrifuging (5,000 rpm, 10 minutes, 4° C.).

TABLE 1

| Modified AGS medium components | (/L) |
| --- | --- |
| L-arginine | 1 g |
| $K_2HPO_4$ | 1 g |
| NaCl | 1 g |
| $MgSO_4 \cdot 7H_2O$ | 0.5 g |
| $Fe_2(SO_4)_3 \cdot 6H_2O$ | 10 mg |
| $CuSO_4 \cdot 5H_2O$ | 1 mg |
| $ZnSO_4 \cdot 7H_2O$ | 1 mg |
| $MnSO_4 \cdot 4H_2O$ | 1 mg |

DNA was extracted from the collected bacterial cells using a DNA extraction kit (ISOIL for Beads Beating, manufactured by Nippon Gene Co., Ltd.). One μg of the extracted DNA was subjected to shotgun sequencing of the genomic DNA using a GS FLX+ 454 manufactured by Roche Diagnostics Ltd.

Genomic DNA sequencing of the compost culture sample SD5AH4G yielded a whole genome sequence (WGS) data set having an average read length of 532 bp, a total read number of 2,471,267, and a total quantity of sequenced genomes of 1.324 Gbp.

<2> Assembly and Statistics of Genomic Data from Compost Culture Sample

The output from the Roche 454 (sff file) was subjected to a second base calling using PyroBayes (Quinlan et al., Nature Methods, 2008, vol. 5, pp. 179 to 181), and a FASTA format sequence file and Quality value file were obtained. Ends were cut from the obtained sequence reads to improve quality, and the reads were assembled using the 454 Life Sciences assembly software Newbler version 2.5.3. Assembly was performed under settings including "minimum acceptable overlap match (mi)=0.9", "option: -large (for large or complex genomes, speeds up assembly but reduces accuracy)".

The total contig length of all contigs assembled to at least 100 bp totaled 38,078,551 bp, and this data set was used for cellulase gene analysis. Of the total read number of 4,942,524 reads, 2,858,018 reads were assembled into contigs having an average of at least 2,617 bp (a total of 14,551 contigs), of which the maximum contig length was 114,826 bp.

<3> Prediction of Glycoside Hydrolase Open Reading Frames (ORFs)

Sequences having EC numbers of 3.2.1.4 (cellulase), 3.2.1.21 (β-glucosidase), 3.2.1.37 ((3-xylosidase), 3.2.1.91 (cellulose 1,4-β-cellobiosidase) and 3.2.1.8 (endo-1,4-β-xylanase) were downloaded (date of access: 2011/12/9) from the UniProt database, and a proteome local database of these glycoside hydrolase genes was constructed. The annotation software MetaGeneAnnotator (Noguchi et al., MetaGeneAnnotator: Detecting Species-Specific Patterns of Ribosomal Binding Site for Precise Gene Prediction in Anonymous Prokaryotic and Phage Genomes, DNA Res., 2008, 15, pp. 387 to 396) was used to predict gene regions (=open reading frames) from the contig sequences obtained in the above section <2>. In order to extract glycoside hydrolase genes from the predicted ORFs, reference was made to the local database using BLASTP (blastall ver. 2.2.18). Furthermore, the option conditions for BLASTP were set such that: "Filter query sequence=false", "Expectation value (E)<1e$^{-20}$" (hereafter, default values were set such that: "Cost to open a gap=−1", "Cost to extended gap=−1", "X dropoff value for gapped alignment=0", "Threshold for extending hits=0", and "Word size=default"), and the hit sequences were collected as glycoside hydrolase genes.

<4> Glycoside Hydrolase (GH) Family Classification of Genes

Functional classification of the sequences collected in section <3> above, including various glycoside hydrolases such as cellulases, endohemicellulases and debranching enzymes, was performed with reference to the protein functional domain sequence database Pfam HMMs (Pfam version 23.0 and HMMER v2.3; Finn et al., Nucleic Acids Research Database, 2010, Issue 38, pp. D211 to 222). Specifically, the glycoside hydrolase (GH) family of each sequence was determined on the basis of homology with the Pfam domain database by using the protein motif search program HMMER (Durbin et al., "The theory behind profile HMMs. Biological sequence analysis: probabilistic models of proteins and nucleic acids", 1998, Cambridge University Press; hmmpfam (Ver. 2.3.2), E-value cutoff <1e$^{-5}$; Database=Pfam_fs (models that can be used to find fragments of the represented domains in a sequence)).

Based on homology search results by BLASTP and reference to Pfam HMMs using the sequence data from the compost culture sample SD5AH4G, 15 ORFs (8 full-length ORFs and 7 partial length ORFs) were predicted as being either cellobiohydrolase genes or endoglucanase genes. The GH family classification results of these 15 genes are shown in Table 2. ORFs for which the coverage of the GH catalytic domain sequence was 70% or greater were counted. As shown in Table 2, from the genome SD5AH4G, two full-length ORFs belonging to the GH family 5, two full-length ORFs in which a domain belonging to GH family 6 and a domain belonging to GH family 5 were linked, and one full-length ORF belonging to each of GH family 9, GH family 12, GH family 26 and GH family 48 were obtained. Primers were designed for all of these ORFs, and the genes were cloned from the compost culture sample-derived DNA by PCR. As a result, the glycoside hydrolase gene SD5AH4G-4A-17 was isolated from the open reading frame SD5AH4G-4 having a sequence in which a domain belonging to GH family 6 and a domain belonging to GH family 5 were linked.

TABLE 2

|  | GH5 | GH6 | GH6 + GH5 | GH9 | GH12 | GH26 | GH48 | Total |
|---|---|---|---|---|---|---|---|---|
| Full-length ORFs | 2 | 0 | 2 | 1 | 1 | 1 | 1 | 8 |
| Partial length ORFs | 0 | 1 | 0 | 4 | 0 | 0 | 2 | 7 |
| Total | 2 | 1 | 2 | 5 | 1 | 1 | 3 | 15 |

<5> Open Reading Frame SD5AH4G-4

The open reading frame SD5AH4G-4 encoded a polypeptide (SEQ ID NO: 1) composed of 863 amino acid residues, and this polypeptide was an amino acid sequence that lacked a stop codon, in which the amino acid residue at position 1 started from a methionine (M) and the 3'-end ended with a linker sequence. It was predicted that the 435 amino acid residues from the tryptophan (W) at position 51 through to the isoleucine (I) at position 485 represented a GH family 6 domain, and this sequence exhibited sequence homology of 76% with the exoglucanase A from the Proteobacterium *Stigmatella aurantiaca* (Genbank: WP_002613368.1). Further, it was predicted that the 294 amino acid residues, linked via a linker, from the valine (V) at position 530 through to the arginine (R) at position 823 represented a GH family 5 domain, and this sequence exhibited sequence homology of 73% with the endoglucanase from the Firmicutes bacterium *Paenibacillus* subspecies KSM-N145 (Genbank: BAF62085.1). The sequence homology values were each calculated using the ClustalW algorithm. Although amino acid sequences exist which exhibit homology with each of the domains, no amino acid sequence having a GH family 5 endoglucanase catalytic domain following a GH family 6 cellobiohydrolase catalytic domain has previously been reported, and the open reading frame SD5AH4G-4 is a completely novel sequence. A secretory signal sequence was not predicted in the open reading frame SD5AH4G-4 by the secretory signal prediction software (SignalP 4.1).

FIG. 1 shows the alignment of the amino acid sequence (SEQ ID NO: 1) predicted from the open reading frame SD5AH4G-4 and the amino acid sequence (SEQ ID NO: 6) of the exoglucanase A from *Stigmatella aurantiaca*, whereas FIG. 2 shows the alignment of the amino acid sequence (SEQ ID NO: 1) predicted from the open reading frame SD5AH4G-4 and the amino acid sequence (SEQ ID NO: 7) of the endoglucanase from *Paenibacillus* subspecies KSM-N145. In FIG. 1 and FIG. 2, the amino acids shown in white on black are the amino acid residues identical to both amino acid sequences, whereas "-" indicates a gap in a sequence.

<6> Gene Cloning

Using a forward primer including a nucleotide sequence represented by SEQ ID NO: 5 (5'-CACCATGGAGGTTTT-GTGGGTTGGT-3': wherein four nucleotides (CACC) were added to the 5'-end of the nucleotide sequence represented by SEQ ID NO: 3, the CACC at the 5'-end in the sequence being a sequence used for vector insertion), and a reverse primer including a nucleotide sequence represented by SEQ ID NO: 4 (5'-TTAACCGCTCGCGCTAGGCGTC-3'), PCR was conducted using a template composed of DNA derived from a compost culture sample that had been amplified using a genome DNA amplification kit (GenomiPhi V2 DNA Amplification Kit, manufactured by GE Healthcare, Inc.). The nucleotide sequence represented by SEQ ID NO: 3 is homologous (identical) with the partial sequence composed of the nucleotides from positions 1 to 21 of the nucleotide sequence represented by SEQ ID NO: 2. Further, the nucleotide sequence represented by SEQ ID NO: 4 is complementary with the partial sequence composed of the nucleotides from positions 2,571 to 2,589 of the nucleotide sequence represented by SEQ ID NO: 2. The amplified PCR product was inserted into a pET101/D-TOPO vector of a Champion pET Directional TOPO Expression Kit (manufactured by Life Technologies Inc.), and transformed into a One Shot TOP10 strain. Positive clones were selected by colony PCR and cultured in an LB liquid medium containing 100 mg/L of ampicillin at a temperature of 37° C. and 200 rpm for 17 to 20 hours, and then plasmids were prepared using a miniprep kit (Wizard plus SV Minipreps DNA Purification System, manufactured by Promega Corporation). Sequence confirmation of the prepared plasmids was performed using a sequencer (3730 DNA Analyzer, manufactured by Life Technologies Corporation).

PCR cloning was used to obtain three gene clones SD5AH4G-4A-17, SD5AH4G-4A-44 and SD5AH4G-4A-45 from the open reading frame SD5AH4G-4. The nucleotide sequence (SEQ ID NO: 2) of the thermostable glycoside hydrolase candidate gene clone SD5AH4G-4A-17, which had cellobiohydrolase activity and endoglucanase activity, included 2,589 bp in a similar manner to the open reading frame SD5AH4G-4, and was completely identical with the predicted ORF.

<7> Expression and Purification of Thermostable Glycoside Hydrolase Protein

A protein having an added histidine tag at the C-terminal was used for purification of the enzyme protein. By inserting the thermostable glycoside hydrolase candidate gene SD5AH4G-4A-17 from which the stop codon had been removed into the aforementioned pET101/D-TOPO vector, a plasmid was obtained containing the SD5AH4G-4A-17 gene to which a histidine tag had been added, and the thus obtained plasmid was introduced into *E. coli* for protein expression using the heat shock method. The Rosetta-gamiB (DE3) pLysS strain (manufactured by Merck & Co., Inc.) was used as the competent cell for the transformation. Expression of the target protein was induced by inoculating the *E. coli* having the target gene into an LB medium containing 100 mg/L of ampicillin, culturing to about $OD_{600}$=0.2 to 0.8, subsequently adding IPTG (isopropyl-β-D(-)-thiogalactopyranoside), and performing additional culturing for 5 to 20 hours. Following culturing, the *E. coli* was collected by centrifugation, and an amount of 50 mM Tris-HCl buffer (pH 8) equivalent to 1/10 of the volume of the culture liquid was added and suspended. Subsequently, a process consisting of 5 minutes disrupting and then 5 minutes of rest was repeated 7 or 8 times using an ultrasonic disrupter Astrason 3000 (manufactured by MISONIX Inc.), thus obtaining a crude extract of the gene recombinant *E. coli* containing the target protein. This gene recombinant *E. coli* crude extract was filtered through a filter (pore size φ=0.45 µm, manufactured by EMD Millipore Corporation), and the resulting filtrate was used as a gene recombinant *E. coli* homogeneous supernatant.

The gene recombinant *E. coli* homogeneous supernatant was loaded onto an ion exchange column HiTrap Q HP (manufactured by GE Healthcare, Inc.) equilibrated with a 50 mM Tris-HCl buffer (pH 8.0), and a medium-high pressure liquid chromatography system AKTA design (manufactured by GE Healthcare, Inc.) was used to fractionate proteins with a concentration gradient of 0 to 50% in a 50 mM Tris-HCl buffer (pH 8.0) containing 1 M of NaCl. The fractions exhibiting cellobiohydrolase activity were pooled, and a centrifugal ultrafiltration membrane VIVASPIN 20 (manufactured by Sartorius stedim Biotech SA) was used to exchange the buffer to a 50 mM Tris-HCl buffer (pH 8.0) containing 750 mM of ammonium sulfate. The fractions with cellobiohydrolase activity following the buffer exchange were loaded onto a hydrophobic interaction separation column HiTrap Phenyl HP (manufactured by GE Healthcare, Inc.) equilibrated with the same buffer solution, and the proteins were fractionated with a concentration gradient of 0 to 100% in a 50 mM Tris-HCl buffer (pH 8.0). The fractions exhibiting cellobiohydrolase activity were pooled and then concentrated using the VIVASPIN 20 until the liquid volume reached about 8 mL. The concentrated sample was loaded onto a gel filtration column Hiload 26/60 superdex 200 pg (manufactured by GE Healthcare, Inc.) equilibrated with a 50 mM Tris-HCl buffer (pH 8.0) containing 150 mM of NaCl, and was fractionated by passing a volume of the same buffer equivalent to 1 to 1.5 times the column volume through the column at a flow rate of 2 to 3 mL/min. The fractions exhibiting cellobiohydrolase activity were pooled, a buffer exchange to a 1 mM phosphate buffer (pH 6.8) and subsequent concentration were performed using the VIVASPIN 20, the concentrated sample was loaded onto a hydroxyapatite column CHT5-1 (manufactured by Bio-Rad Laboratories, Inc.) equilibrated with the same buffer, and the proteins were fractionated with a concentration gradient of 0 to 100% in a 400 mM phosphate buffer (pH 6.8). The fractions exhibiting cellobiohydrolase activity were once again pooled, and a buffer exchange to a 50 mM Tris-HCl buffer (pH 8.0) and subsequent concentration were performed, yielding a purified enzyme with a final concentration of about 1 mg/mL.

The gene recombinant *E. coli* homogenous supernatant and the purified enzyme (purified thermostable glycoside hydrolase protein) were checked by SDS-PAGE (SDS-polyacrylamide gel electrophoresis) analysis. Electrophoresis samples obtained by mixing 5 µg of the supernatant or 0.5 µg of the purified enzyme with a sample buffer 4-fold concentrate containing 2-mercaptoethanol (manufactured by Wako Pure Chemical Industries, Ltd.) at 1:1 were each treated at 95° C. for 4 minutes, and SDS-PAGE was then performed using a 10% Criterion TGX stain-free gel (manufactured by Bio-Rad Laboratories, Inc.). Following completion of the electrophoresis, the protein bands were visualized using the imaging system ChemiDoc (manufactured by Bio-Rad Laboratories, Inc.).

FIG. 3 shows the SDS-PAGE analysis results of the gene recombinant *E. coli* homogenous supernatant prepared from the transformed *E. coli* into which the SD5AH4G-4A-17 gene had been introduced, and the purified enzyme prepared from the gene recombinant *E. coli* homogenous supernatant. The figure shows an electrophoretic pattern in which lane 1 represents a protein mass marker, lane 2 represents the gene recombinant *E. coli* homogenous supernatant, and lane 3 represents the purified enzyme. The results revealed a strong band in the gene recombinant *E. coli* homogenous supernatant (lane 2) near the mass of 96.7 kDa expected from the amino acid sequence (SEQ ID NO: 1) and the pET101/D-TOPO vector histidine tag, and a single band corresponding with this band (indicated by an arrow in the figure) was observed in the purified enzyme (lane 3).

<8> Measurement of Cellobiohydrolase Activity Against PSA Substrate

The cellobiohydrolase activity of the enzyme protein (SD5AH4G-4A-17) encoded by the SD5AH4G-4A-17 gene against a substrate of PSA was investigated. In the measurements, a solution prepared by diluting the purified enzyme obtained in section <7> above with a 0.05 M Tris-HCl buffer (pH 8.0) to obtain a concentration of 1 mg/mL was used.

The PSA used as the substrate was prepared by first dissolving an Avicel powder (microcrystalline cellulose powder, manufactured by Merck & Co., Inc.) in a phosphoric acid solution, subsequently adding purified water to cause precipitation, and then washing until a pH of 5 or higher was obtained. The PSA used in the experiments described below was all prepared by this method.

A sample tube with a volume of 2.0 mL was used as the reaction vessel, and the reaction solution was composed of 15 μL of the diluted purified enzyme, 10 μL of purified water, 25 μL of a 200 mM acetate buffer (pH 4.0), and 50 μL of a 1% by mass PSA solution. In all measurements, a mixed solution prepared by replacing the purified enzyme solution with a 50 mM Tris-HCl buffer (pH 8.0) and then reacting the solution under the same conditions was used as a control. Further, the substrate solution and a mixed solution of the purified enzyme solution, the purified water and the buffer were held separately at the reaction temperature for five minutes (pre-incubation) before being mixed to initiate the reaction.

During reaction, all of the mixed solutions were adjusted to the prescribed temperature using a Thermomixer (manufactured by Eppendorf AG). Following completion of the 15- to 20-minute reaction, 3,5-dinitrosalicylic acid reagent (DNS solution) was added to each mixed solution in a volume equal to that of the solution, and the resulting mixture was heated at 100° C. for 5 minutes, cooled for 5 minutes on ice, and then centrifuged at 17,500 g for 5 minutes at room temperature to obtain a supernatant. The amount of reducing sugars within the supernatant was determined by measuring the absorbance at 540 nm using a spectrophotometer, calculating the amount of reducing sugars using a calibration curve prepared with glucose, and then calculating the amount of reducing sugars produced by the enzymatic hydrolysis based on the difference from the control. The enzymatic activity for producing 1 μmol of reducing sugars per minute was defined as 1 U, and the value obtained by dividing this activity by the amount of protein was defined as the specific activity (U/mg). Each measurement was performed for three independent experiments, and a mean value and a standard error were determined.

<9> Endoglucanase Activity Against CMC Substrate

The endoglucanase activity of the enzyme protein SD5AH4G-4A-17 against a substrate of CMC (manufactured by Sigma-Aldrich Co. LLC.) was investigated. In the measurements, with the exception of using a reaction solution composed of 15 μL of the diluted purified enzyme, 10 μL of purified water, 25 μL of a 200 mM McIlvaine buffer (pH 4.0), and 50 μL of a 1% by mass CMC solution, the same procedure as that described above in section <8> was used to determine the amount of reducing sugars produced by the enzymatic hydrolysis and then calculate the specific activity (U/mg).

<10> Substrate Specificity of SD5AH4G-4A-17

The hydrolysis activity of the enzyme protein SD5AH4G-4A-17 against various cellulose substrates and hemicellulose substrates was investigated. For the substrates, PSA, Avicel powder, CMC (manufactured by Sigma-Aldrich Co. LLC.), xylan (derived from beech wood, manufactured by Sigma-Aldrich Co. LLC.), lichenan (manufactured by MP Biomedicals, LLC), laminarin (derived from *Laminaria digitata*, manufactured by Sigma-Aldrich Co. LLC.), PNPC (p-nitrophenyl-β-D-cellobioside, manufactured by Sigma-Aldrich Co. LLC.) and PNPG (p-nitrophenyl-β-D-glucopyranoside, manufactured by Sigma-Aldrich Co. LLC.) were used.

When PSA, Avicel powder, CMC, xylan, lichenan or laminarin was used as the substrate, with the exceptions of adding 50 μL of a 1% by mass aqueous solution of the substrate to the reaction solution and setting the reaction temperature to 50° C., measurement of the hydrolysis activity was performed in the same manner as that described above in section <8>, the amount of reducing sugars produced by the enzymatic hydrolysis was determined, and the specific activity (U/mg) was calculated. For the xylan measurement, a calibration curve prepared using xylose was used.

When PNPC or PNPG was used as the substrate, with the exceptions of first adding 50 μL of a 3.4 mM aqueous solution of the substrate to the reaction solution, setting the reaction temperature to 50° C., and setting the reaction time to 20 minutes, measurement of the hydrolysis activity was performed by conducting the enzyme reaction in the same manner as that described above in section <8>. Following completion of the reaction, an equal volume of a 200 mM aqueous solution of sodium carbonate was added to the reaction solution, and the resulting mixture was then centrifuged for 5 minutes to obtain a supernatant. The amount of p-nitrophenol in the supernatant was determined by measuring the absorbance at 420 nm using a spectrophotometer and calculating the amount of p-nitrophenol in the supernatant using a calibration curve prepared with p-nitrophenol. The enzymatic activity for producing 1 μmol of p-nitrophenol per minute was defined as 1 U, and the value obtained by dividing this activity by the amount of protein was defined as the specific activity (U/mg).

Figure 4:
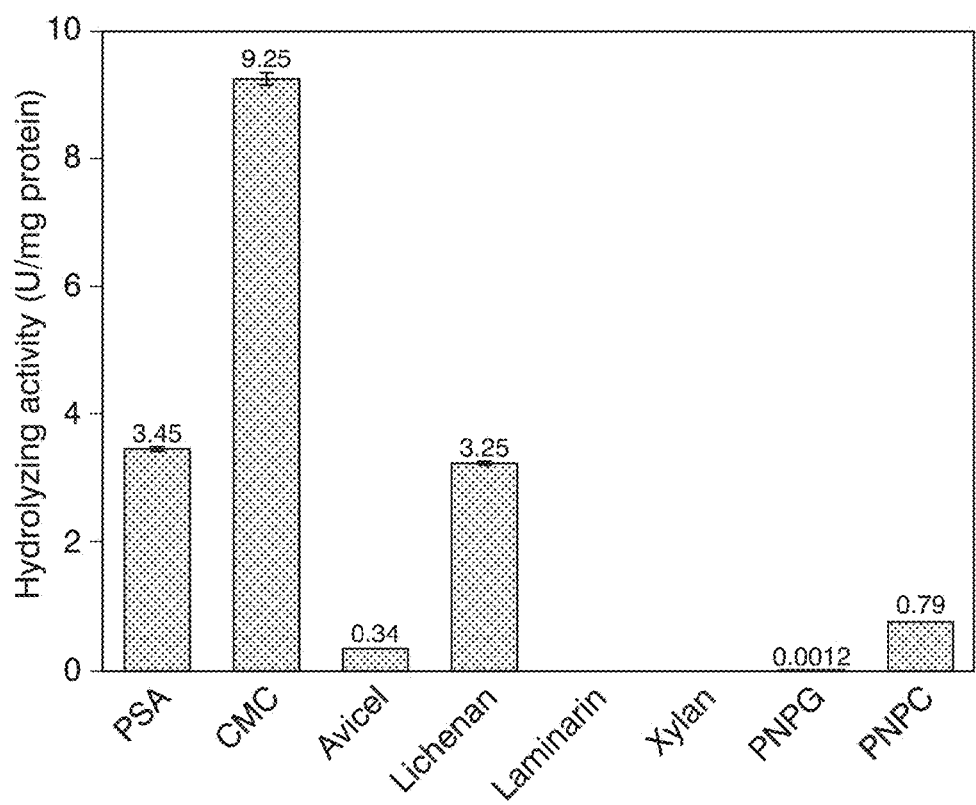
FIG. 4 is a diagram showing the results of measuring the hydrolysis activity against various substrates of the SD5AH4G-4A-17 protein obtained by expressing the SD5AH4G-4A-17 gene in *E. coli* in Example 1.

The measurement results are shown in FIG. 4. The results revealed that SD5AH4G-4A-17 exhibited hydrolysis activity against PSA, CMC, lichenan and PNPC and also exhibited weak hydrolysis activity against Avicel and PNPG, but exhibited almost no hydrolysis activity against laminarin and xylan.

<11> Temperature and pH Dependencies of Cellobiohydrolase Activity and Endoglucanase Activity of SD5AH4G-4A-17

The temperature dependency of the PSA hydrolysis activity of SD5AH4G-4A-17 was investigated. Specifically, with the exception of setting the reaction temperature to 20, 30, 40, 50, 60, 65, 70, 75, 80 or 85° C., reaction was performed in the same manner as that described above in section <8>, and for each temperature, the amount of reducing sugars produced by the enzymatic hydrolysis was determined, and the PSA hydrolysis activity (U/mg) was calculated.

Further, measurements were also performed using reaction solutions in which a 10 mM aqueous solution of $CaCl_2$ was added instead of the 10 μL of purified water, and for each temperature, the amount of reducing sugars produced by the enzymatic hydrolysis was determined, and the PSA hydrolysis activity (U/mg) was calculated.

Figure 5:
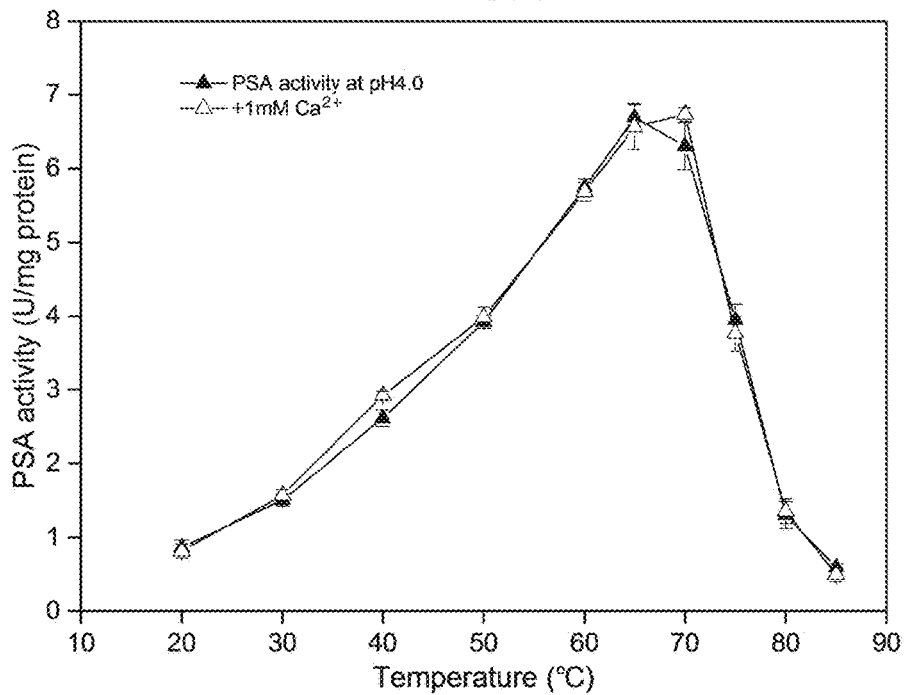
FIG. 5 is a diagram showing the results of measuring the PSA hydrolysis activity (pH 4.0) at various temperatures, either in the presence of calcium ions or in the absence of calcium ions, of the SD5AH4G-4A-17 protein obtained by expressing the SD5AH4G-4A-17 gene in *E. coli* in Example 1.

The results are shown in FIG. 5. SD5AH4G-4A-17 exhibited PSA hydrolysis activity in a temperature range from 20 to 85° C. The optimum temperature ($T_{opt}$) at which the highest activity was observed was 65° C. in the absence of calcium ions (labeled "PSA activity at pH 4.0" in the figure) and 70° C. in the presence of calcium ions (labeled "+1 mM $Ca^{2+}$" in the figure).

The temperature dependency of the CMC hydrolysis activity of SD5AH4G-4A-17 was also investigated. Specifically, with the exception of setting the reaction temperature to 30, 40, 50, 60, 70, 80, 90 or 100° C., reaction was performed in the same manner as that described above in section <9>, and for each temperature, the amount of reducing sugars produced by the enzymatic hydrolysis was determined and the CMC hydrolysis activity (U/mg) was calculated.

Figure 6:
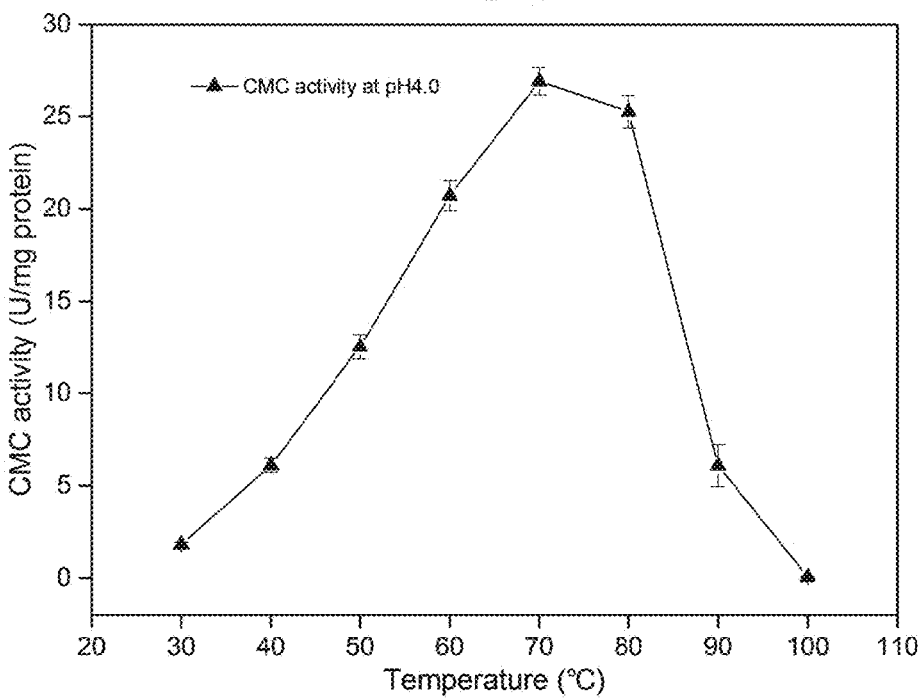
FIG. 6 is a diagram showing the results of measuring the CMC hydrolysis activity (pH 4.0) at various temperatures of the SD5AH4G-4A-17 protein obtained by expressing the SD5AH4G-4A-17 gene in *E. coli* in Example 1.

The results are shown in FIG. 6. SD5AH4G-4A-17 exhibited CMC hydrolysis activity in a temperature range from 30 to 90° C. The optimum temperature ($T_{opt}$) at which the highest activity was observed was 70° C.

The pH dependency of the PSA hydrolysis activity of SD5AH4G-4A-17 was investigated. Specifically, with the exception of performing the reaction at 50° C. using a 200 mM glycine hydrochloride buffer (glycine-HCl, pH 2.2 to 3.0), a McIlvaine buffer (MB, pH 3 to 8), an acetate buffer (SAB, pH 3.5 to 6), a 200 mM phosphate buffer (PB, pH 6 to 8) or a Tris hydrochloride buffer (Tris-HCl, pH 8 to 9), reaction was performed in the same manner as that described above in section <8>, and for each pH value, the amount of reducing sugars produced by the enzymatic hydrolysis was determined and the PSA hydrolysis activity (U/mg) was calculated.

Figure 7:
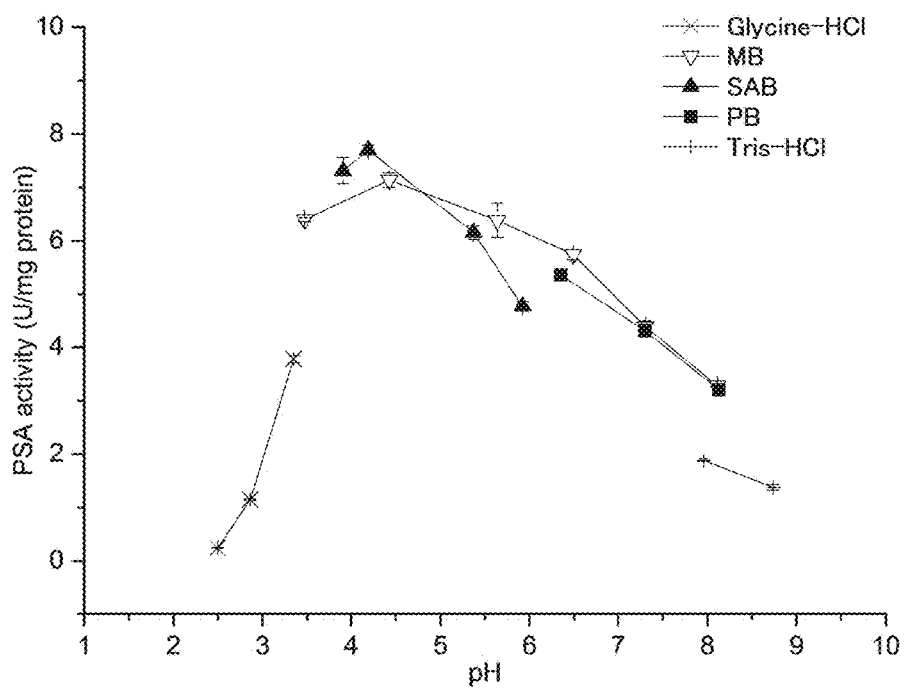
FIG. 7 is a diagram showing the results of measuring the PSA hydrolysis activity (50° C.) at various pH values of the SD5AH4G-4A-17 protein obtained by expressing the SD5AH4G-4A-17 gene in *E. coli* in Example 1.

The measurement results are shown in FIG. 7. For the pH values, the actual measurement value obtained for the mixed solution containing the substrate, the buffer and the enzyme was plotted. SD5AH4G-4A-17 exhibited PSA hydrolysis activity in a pH range from pH 3 to 9. The optimum pH was 4.19 (actual measurement value for the mixed solution containing the substrate, the buffer and the enzyme).

The pH dependency of the CMC hydrolysis activity of SD5AH4G-4A-17 was also investigated. Specifically, with the exception of performing the reaction at 50° C. using a 200 mM glycine hydrochloride buffer (glycine-HCl, pH 2.6 to 3.0), a McIlvaine buffer (MB, pH 3 to 8), or a Tris hydrochloride buffer (Tris-HCl, pH 8 to 9), reaction was performed in the same manner as that described above in section <9>, and for each pH value, the amount of reducing sugars produced by the enzymatic hydrolysis was determined and the CMC hydrolysis activity (U/mg) was calculated.

Figure 8:
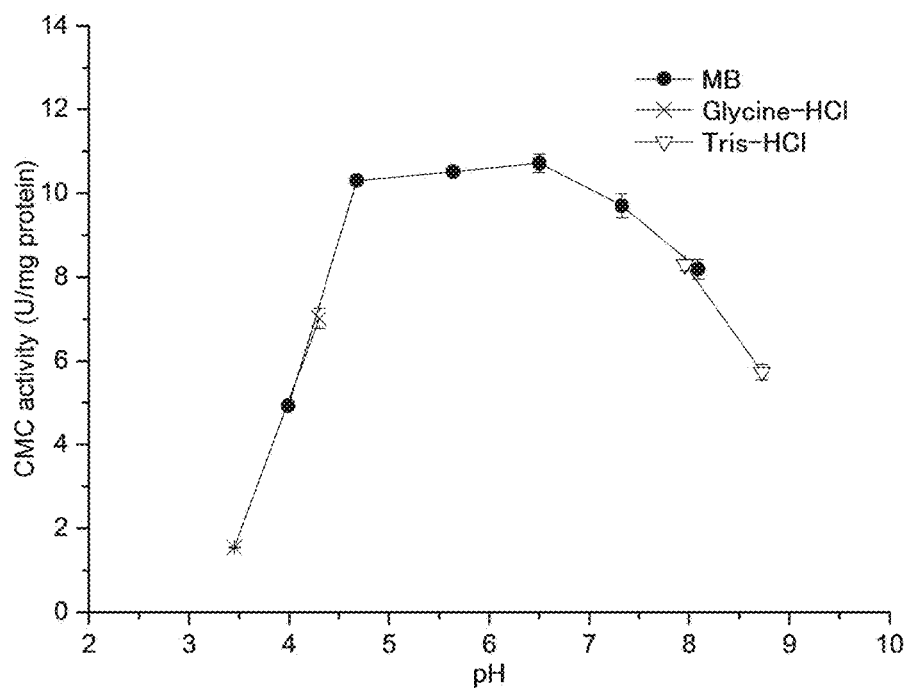
FIG. 8 is a diagram showing the results of measuring the CMC hydrolysis activity (50° C.) at various pH values of the SD5AH4G-4A-17 protein obtained by expressing the SD5AH4G-4A-17 gene in *E. coli* in Example 1.

The measurement results are shown in FIG. 8. For the pH values, the actual measurement value obtained for the mixed solution containing the substrate, the buffer and the enzyme was plotted. SD5AH4G-4A-17 exhibited CMC hydrolysis activity in a pH range from pH 3.5 to 9. The optimum pH had a broad range from 4.68 to 6.5 (actual measurement values for the mixed solutions containing the substrate, the buffer and the enzyme).

<12> Thermal Stability Measurement of Glycoside Hydrolase by Differential Scanning Fluorimetry Differential scanning fluorimetry (DSF) is one of the methods of measuring the thermal denaturation of proteins using a fluorescent dye and a real-time PCR machine, and can be applied to all manner of proteins. The fluorescent dyes used in DSF such as SYPRO Orange emit fluorescence under nonpolar conditions when bound to a hydrophobic region, while the emission is suppressed under the polar conditions produced upon dissolution in water. Usually, the protein structure unfolds at the thermal denaturation temperature, and the internal hydrophobic regions of the protein are exposed at the protein surface. When SYPRO Orange binds to such an exposed hydrophobic region, excitation light having a wavelength of 470 to 480 nm causes emission of a strong fluorescence having a peak near a wavelength of 595 nm. By increasing the temperature of the protein solution at regular intervals in a stepwise manner and measuring the fluorescence intensity, the thermal denaturation temperature (=change point of the fluorescence intensity) can be calculated.

Measurements were performed using a purified enzyme solution prepared by dissolving the purified enzyme SD5AH4G-4A-17 obtained in section <7> above in water at a concentration of 1 mg/mL.

Specifically, 2 µL of 100-fold diluted SYPRO Orange (manufactured by Life Technologies Inc.), 1 µL of the purified enzyme solution with a concentration of 1 mg/mL, 5 µL of a 200 mM acetate buffer (pH 4.0), and 12 µL of purified water, a 1:1 mixed solution of purified water and a 10 mM $CaCl_2$ solution or a 2:1 mixed solution of purified water and a 50 mM EDTA solution were added to each well of a 96-well PCR plate (Multiplate 96 Well PCR Plate MLL-9651, manufactured by Bio-Rad Laboratories, Inc.) so that the volume in each well was 20 µL. The PCR plate was sealed with Optical Flat 8-Cap Strips (manufactured by Bio-Rad Laboratories, Inc.), the temperature of each well was increased in steps of 0.2° C. from 30° C. up to 100° C. using a real-time PCR machine (CFX96 Touch Real-Time PCR System, manufactured by Bio-Rad Laboratories, Inc.), and following a pause of 10 seconds after each target temperature was achieved, the fluorescence intensity of each well was measured simultaneously. The SYPRO Orange was excited by a light emitting diode (LED) having a wavelength range of 450 to 490 nm, the emitted light from the SYPRO Orange was passed through a band pass filter having a range of 560 to 580 nm, a CCD camera was used to measure the fluorescence intensity, and the change in fluorescence intensity was plotted as a function of the temperature. The thermal denaturation temperature (melting temperature: Tm) was defined as the value at the local minimum of the first derivative of the fluorescence intensity curve as a function of temperature (namely, "−d(Fluorescence)/dt" shown along the Y axis of FIG. 9B).

Data analysis was conducted using the analysis software CFX Manager (manufactured by Bio-Rad Laboratories, Inc.) supplied with the real-time PCR machine. Each measurement was performed for three independent experiments, and a mean value and a standard error were determined.

Figure 9:
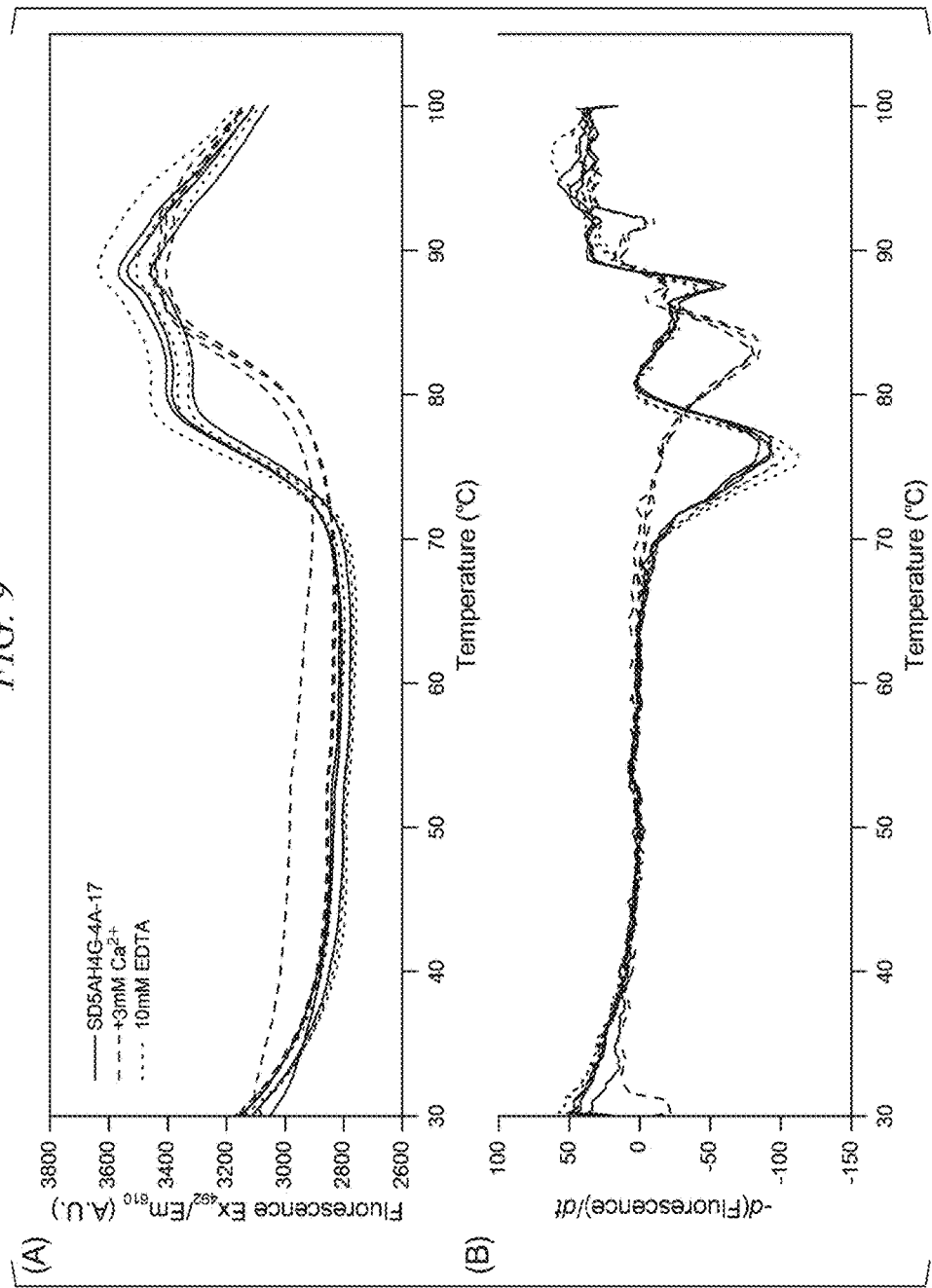
FIG. 9 (A) is a diagram showing actual measurement data for the change in the fluorescence intensity of SYPRO Orange that is generated in association with the thermal denaturation exhibited by the SD5AH4G-4A-17 protein obtained by expressing the SD5AH4G-4A-17 gene in *E. coli* in Example 1.

FIG. 9 (A) shows the actual measurement data for the change in the fluorescence intensity of SYPRO Orange measured by the DSF method and caused in association with the thermal denaturation exhibited by the SD5AH4G-4A-17 enzyme protein. FIG. 9(B) shows the first derivative "−d (Fluorescence)/dt" of the fluorescence intensity change curve of FIG. 9(A).

The first derivative of the fluorescence intensity of SD5AH4G-4A-17 had a local minimum near 76° C., indicating that thermal denaturation occurs at that temperature. Further, under the conditions including added $CaCl_2$, the local minimum occurred near 83° C. On the other hand, under the conditions including added EDTA, the local minimum was hardly changed.

The average values for the melting temperature Tm were 76.5±0.4° C. (no $CaCl_2$ addition), 82.9±0.2° C. (3 mM $CaCl_2$ addition) and 75.5±0.3° C. (10 mM EDTA addition), and it is confirmed that the thermal denaturation temperature was raised 6.4° C. by a $CaCl_2$ addition.

[Sequence Listings]

The invention claimed is:

1. A polypeptide comprising a protein having glycoside hydrolase activity and an amino acid sequence that is heterologous to the protein having glycoside hydrolase activity, wherein the amino acid sequence of the protein having glycoside hydrolase activity comprises the amino acid sequence of SEQ ID NO: 1, and wherein the heterologous amino acid sequence is selected from the group consisting of a cellulose-binding module, a linker, a signal peptide and a purification tag.

2. The polypeptide according to claim 1, which, in the presence of calcium ions, exhibits hydrolysis activity against a substrate of phosphoric acid swollen Avicel and hydrolysis activity against a substrate of carboxymethyl cellulose at least under conditions of 70° C. and pH 4.0.

3. A glycoside hydrolase mixture, comprising the polypeptide according to claim 1 and at least one other glycoside hydrolase.

4. A glycoside hydrolase mixture, comprising the polypeptide of claim 2 and at least one other glycoside hydrolase.

5. A method for producing a cellulose degradation product, the method comprising contacting a material comprising cellulose with the polypeptide according to claim 1, to thereby produce a cellulose degradation product.

6. A method for producing a cellulose degradation product, the method comprising contacting a material comprising cellulose with the polypeptide according to claim 2, to thereby produce a cellulose degradation product.

7. A method for producing a cellulose degradation product, the method comprising contacting a material comprising cellulose with the glycoside hydrolase mixture according to claim 3, to thereby produce a cellulose degradation product.

8. A method for producing a cellulose degradation product, the method comprising contacting a material comprising cellulose with the glycoside hydrolase mixture according to claim 4, to thereby produce a cellulose degradation product.

* * * * *

```
                         SEQUENCE LISTING

<160> NUMBER OF SEQ ID NOS: 7

<210> SEQ ID NO 1
<211> LENGTH: 863
<212> TYPE: PRT
<213> ORGANISM: Unknown
<220> FEATURE:
<223> OTHER INFORMATION: Amino acid sequence of SD5AH4G-4A-17

<400> SEQUENCE: 1

Met Glu Val Leu Trp Val Gly Phe Gly Lys Lys Glu Ser Met Arg Asn
1               5                   10                  15

Gln Thr Lys Glu Gly Ser Asp Thr Gly Met Thr Met Ala Trp Lys Gln
            20                  25                  30

Arg Ser Gly Leu Ile Ala Leu Ile Leu Ala Leu Val Ala Gly Leu Leu
        35                  40                  45

Leu Pro Trp Gly Ser Leu Pro Lys Ala Ala Ala Glu Pro His Val Asp
    50                  55                  60

Asn Pro Phe Val Gly Ala Thr Ala Tyr Val Asn Pro Asp Tyr Ala Ala
65                  70                  75                  80

Leu Val Asp Ser Ser Ile Ala Arg Val Ser Asp Pro Thr Leu Ala Ala
                85                  90                  95

Lys Met Arg Thr Val Lys Thr Tyr Pro Thr Ala Val Trp Leu Asp Arg
            100                 105                 110

Ile Ala Ala Ile Asp Gly Gly Pro Gly Arg Arg Ser Leu Val Gln His
        115                 120                 125

Leu Asp Thr Ala Leu Ala Gln Lys Gln Gly Asn Thr Pro Ile Thr Ala
    130                 135                 140

Met Phe Val Ile Tyr Asn Met Pro Gly Arg Asp Cys Ala Ala Leu Ala
145                 150                 155                 160

Ser Asn Gly Glu Leu Pro Leu Thr Gln Glu Gly Leu Gln Arg Tyr Lys
                165                 170                 175

Thr Glu Tyr Ile Asp Arg Ile Ala Ala Ile Phe Ala Asp Pro Lys Tyr
            180                 185                 190

Ala Gly Ile Arg Ile Val Thr Val Ile Glu Pro Asp Gly Leu Pro Asn
        195                 200                 205

Leu Val Thr Asn Leu Ser Asp Pro Glu Cys Ala Gln Ala Asn Ser Ser
    210                 215                 220

Gly Ile Tyr Val Glu Ala Val Arg Tyr Ala Ile Asn Lys Leu Ser Glu
225                 230                 235                 240

Ile Pro Asn Val Tyr Ile Tyr Leu Asp Ile Ala His Ser Gly Trp Leu
                245                 250                 255

Gly Trp Asp Asn Asn Arg Thr Gly Ala Val Gln Leu Tyr Thr Asn Val
            260                 265                 270

Val Arg Gly Thr Thr Lys Gly Leu Ser Ser Val Asp Gly Phe Val Thr
        275                 280                 285

Asn Val Ala Asn Tyr Thr Pro Leu Glu Glu Pro Tyr Leu Thr Asp Pro
    290                 295                 300

Asn Leu Thr Val Gly Gly Gln Pro Leu Lys Ser Ala Lys Phe Tyr Glu
305                 310                 315                 320

Trp Asn Pro Tyr Phe Asp Glu Val Asp Tyr Ala Ala Ala Leu Arg Ser
                325                 330                 335

Ala Phe Ile Ser Ala Gly Trp Pro Thr Ser Ile Gly Met Leu Ile Asp
            340                 345                 350
```

```
Thr Ser Arg Asn Gly Trp Gly Pro Asn Arg Pro Thr Gly Ala Ser
    355                 360                 365
Gly Thr Thr Val Asp Ala Tyr Val Asn Ser Gly Arg Val Asp Arg Arg
    370                 375                 380
Ala His Arg Gly Leu Trp Cys Asn Val Ser Gly Ala Gly Ile Gly Met
385                 390                 395                 400
Pro Pro Gln Val Ala Pro Ala Ala Tyr Ala Ser Gln Gly Ile Glu Ala
                405                 410                 415
Phe Val Trp Val Lys Pro Pro Gly Glu Ser Asp Gly Ala Ser Ser Glu
                420                 425                 430
Ile Pro Asn Asp Glu Gly Lys Arg Phe Asp Arg Met Cys Asp Pro Thr
            435                 440                 445
Tyr Thr Thr Gln Tyr Gly Val Leu Thr Gly Ala Leu Pro Asn Ala Pro
        450                 455                 460
Leu Ala Gly Gln Trp Phe His Asp Gln Phe Val Met Leu Val Gln Asn
465                 470                 475                 480
Ala Tyr Pro Ala Ile Pro Thr Ser Gly Gly Thr Pro Ala Pro Ser
                485                 490                 495
Ala Thr Ala Thr Pro Thr Pro Thr Pro Thr Pro Thr Pro Ser
            500                 505                 510
Val Thr Pro Thr Pro Ser Val Thr Pro Thr Pro Thr Ser Ser Thr Ser
        515                 520                 525
Phe Val Ala Arg His Gly Gln Leu Arg Val Val Gly Asn Gln Leu Val
    530                 535                 540
Asp Gln Asn Gly Gln Pro Ile Gln Leu Arg Gly Ile Ser Ser His Gly
545                 550                 555                 560
Leu Gln Trp Tyr Gly His Phe Val Asn Arg Asp Ser Leu Arg Trp Leu
                565                 570                 575
Arg Asp Asp Trp Gly Ile Thr Val Phe Arg Ala Ala Leu Tyr Thr Ala
            580                 585                 590
Glu Gln Gly Tyr Ile Thr Asn Pro Ser Leu Lys Glu Lys Val Lys Glu
        595                 600                 605
Ala Val Gln Ala Ala Ile Glu Leu Gly Ile Tyr Val Ile Ile Asp Trp
    610                 615                 620
His Ile Leu Ser Asp Gly Asp Pro Asn Thr Tyr Lys Glu Gln Ala Lys
625                 630                 635                 640
Ala Phe Phe Asp Glu Met Ser Arg Leu Tyr Gly Ser Tyr Pro Asn Val
                645                 650                 655
Ile Tyr Glu Ile Ala Asn Glu Pro Asn Gly Val Thr Trp Glu Gly Gln
            660                 665                 670
Val Lys Pro Tyr Ala Ser Glu Val Ile Pro Val Ile Arg Ala Asn Asp
        675                 680                 685
Pro Asp Asn Leu Ile Ile Val Gly Thr Thr Thr Trp Ser Gln Asp Val
    690                 695                 700
His Leu Ala Ala Asp Ser Pro Leu Pro Tyr Asn Asn Leu Ala Tyr Ala
705                 710                 715                 720
Leu His Phe Tyr Ala Gly Thr His Gly Gln Trp Leu Arg Asp Arg Ile
                725                 730                 735
Asp Tyr Ala Arg Asn Lys Gly Ile Ala Ile Phe Val Ser Glu Trp Gly
            740                 745                 750
Thr Ser Thr Ser Thr Gly Asp Gly Gly Pro Tyr Leu Thr Glu Ser Gln
        755                 760                 765
```

```
Gln Trp Leu Asp Phe Leu Asn Ala Arg Gln Ile Ser Trp Val Asn Trp
        770                 775                 780

Ser Leu Ser Asp Lys Ala Glu Ser Ser Ala Ala Leu Leu Pro Gly Ala
785                 790                 795                 800

Ser Ala Thr Gly Gly Trp Thr Asp Ala Gln Leu Ser Gln Ser Gly Arg
                805                 810                 815

Phe Val Arg Ala Gln Ile Arg Ser Gly Val Leu Thr Pro Thr Pro Ala
            820                 825                 830

Pro Ser Ala Thr Pro Thr Pro Ser Val Thr Pro Thr Val Thr Pro Thr
            835                 840                 845

Ser Thr Pro Thr Pro Thr Pro Thr Pro Thr Pro Ser Ala Ser Gly
            850                 855                 860

<210> SEQ ID NO 2
<211> LENGTH: 2589
<212> TYPE: DNA
<213> ORGANISM: Unknown
<220> FEATURE:
<223> OTHER INFORMATION: Nucleotide sequence encoding the amino acid
      sequence of SD5AH4G-4A-17

<400> SEQUENCE: 2
atggaggttt tgtgggttgg ttttggtaaa aaagaatcca tgaggaacca acgaaagag       60 gggagtgaca caggcatgac gatggcgtgg aaacagcgca gcggattgat cgcgttgatt    120
ttggcattgg tagcgggttt gctgctgcca tggggatcgc tgccgaaagc ggcggcggag    180
ccgcatgtgg acaatccgtt tgtaggagcg acggcttacg tcaatccgga ctatgcggcg    240
ctggtcgatt cgtcgatcgc gagggtgagc gatccaacgc tggcggcgaa gatgcggacg    300
gtcaagacgt atccgacggc ggtgtggctg atcggatcg cggcgattga cggagggccg    360
ggaagacgga gcttggtgca gcatttggat acggcgttgg cgcagaagca agggaatacg    420
ccgattacgg cgatgtttgt gatttacaat atgccgggtc gggactgcgc ggcgctggcg    480
tcgaacgggg agctgccgct gacgcaggaa gggctgcaga ggtacaagac ggagtatatt    540
gaccgaattg cggcaatttt tgcagatccg aagtatgcgg aattcggat cgtgacggtg    600 attgaaccgg acgcttgcc gaacctggtg acgaacctga cgatccgga atgcgcgcag    660 gcgaattcaa gcggaattta tgtagaggca gtacgatatg cgatcaacaa gttgagcgaa    720
attccgaacg tgtatattta cctggacatt gcgcattcgg gatggctggg ctgggacaac    780
aaccggaccg cgcggtgca gctgtatacg aacgtggtgc gagggacgac gaaagggctt    840
tcaagtgtgg acgggtttgt gacgaacgtg gcgaactata cgccgctcga ggagccgtat    900
ttgacggatc cgaacctgac ggtgggtgga cagccgctta agtcagcgaa gttttatgag    960
tggaacccgt attttgatga agtagattat gcggcagcgt tgcggtcggc gtttatcagc   1020
gcggggtggc cgacgagcat cgggatgttg atcgacacga ccgcaacgg ctggggcgga   1080 ccgaaccggc cgacgggagc gagcgggacg acggtggacg cgtatgtgaa ttcgggcgc    1140 gtggaccgtc gggcgcatcg ggggctgtgg tgtaacgtca gcggagcagg gatcgggatg   1200
ccgccgcaag tggcgccggc ggcgtatgcg tcgcaaggga ttgaggcgtt cgtctgggtg   1260
aagccgcccg gggagtcgga cggagcgagt tcggagatac cgaacgacga aggcaagcgg   1320
tttgaccgga tgtgcgatcc gacgtacacg acgcaatacg gggtgttgac gggggcgttg   1380
ccgaacgcgc cgttggcggg gcaatggttc catgatcagt ttgtgatgtt ggtgcagaat   1440
gcgtatccgg cgattccgac gagcggcggc gggacaccgg cgccgagcgc gacggcgacg   1500
```

-continued

| | |
|---|---|
| ccgacaccga cgccgacacc gacaccgacg ccgagtgtga cgccgacgcc gagtgtgacg | 1560 |
| ccaacgccga catcgtcgac aagttttgtg gccaggcacg ggcaattgag agtcgtgggg | 1620 |
| aatcaattgg tcgaccaaaa tggacaaccc atccaactaa gaggcattag ttctcatggg | 1680 |
| ttacaatggt atgggcattt cgtcaatcga gacagcctcc gatggctccg agatgattgg | 1740 |
| ggaataacag ttttccgagc agctctgtat actgccgaac aaggatatat cacgaatccg | 1800 |
| tctttaaaag aaaaagtgaa agaagctgta caagccgcaa ttgagctcgg tatttatgtg | 1860 |
| atcatcgact ggcacatttt gtctgatggc gatccgaaca cgtacaaaga gcaagcgaag | 1920 |
| gcgttttcg acgagatgtc gcgattgtac ggcagttatc cgaacgtgat ttatgagatc | 1980 |
| gccaacgaac cgaatggtgt gacatgggaa ggacaggtta agccgtacgc ttcggaagtg | 2040 |
| attccggtca tccgtgctaa tgaccctgac aatctcatta ttgtcggaac gacaacatgg | 2100 |
| agtcaggatg tccatcttgc ggcagatagc ccgctaccct acaacaacct ggcgtatgct | 2160 |
| ctccatttct atgccggtac gcatggtcaa tggttgagag accggattga ctatgcgagg | 2220 |
| aataaaggta tcgcgatttt cgtgagcgaa tgggggacaa gcacttcgac aggtgatgga | 2280 |
| ggcccctacc tcacagaatc gcaacaatgg ctggatttcc ttaatgctcg gcagatcagt | 2340 |
| tgggtgaact ggtcgttgag cgacaaggcc gagtcatccg cagcattgtt gcctggcgca | 2400 |
| agcgcaacag gtggttggac ggacgcacaa ttgtctcagt cggggcgttt tgtccgcgct | 2460 |
| caaattcgca gcggtgtact gacgcctaca ccggcgccga gcgcgacgcc gacaccgagc | 2520 |
| gtgacaccaa ccgtgacgcc gacgtcgaca ccgacgccga cgcccacacc gacgcctagc | 2580 |
| gcgagcggt | 2589 |

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3

| | |
|---|---|
| atggaggttt tgtgggttgg t | 21 |

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4

| | |
|---|---|
| ttaaccgctc gcgctaggcg tc | 22 |

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5

| | |
|---|---|
| caccatggag gttttgtggg ttggt | 25 |

<210> SEQ ID NO 6
<211> LENGTH: 696
<212> TYPE: PRT
<213> ORGANISM: Stigmatella aurantiaca

<400> SEQUENCE: 6

```
Met Gln Arg Asn Thr Pro Arg Thr Arg Ser Leu Ser Leu Ala Arg Pro
 1               5                  10                  15

Leu Cys Leu Leu Leu Thr Leu Trp Gly Gly Leu Ala Ala Ala Ala Val
            20                  25                  30

His Val Asp Asn Pro Phe Glu Gly Ala Thr Ala Tyr Val Asn Pro Asp
        35                  40                  45

Tyr Ala Leu Ile Asp Thr Ser Ile Ala Lys Thr Thr Asp Ser Thr
50                  55                  60

Leu Ala Ala Lys Met Arg Thr Val Lys Lys Tyr Pro Thr Ala Val Trp
65                  70                  75                  80

Leu Asp Arg Ile Ala Ala Ile His Gly Gly Ser Val Asn Gly Gly Arg
                85                  90                  95

Lys Ser Leu Arg Asp His Leu Asp Leu Val Leu Ala Gln Lys Lys Pro
                100                 105                 110

Gly Gln Pro Ile Thr Ala Thr Phe Val Ile Tyr Asp Met Pro Gly Arg
                115                 120                 125

Asp Cys Ala Ala Leu Ala Ser Asn Gly Glu Leu Pro Leu Thr Pro Ala
130                 135                 140

Gly Leu Gln Arg Tyr Lys Ala Glu Tyr Ile Asp Ala Ile Ala Ala Val
145                 150                 155                 160

Leu Ala Asp Pro Val Tyr Gln Asp Ile Arg Ile Ile Thr Val Ile Glu
                165                 170                 175

Pro Asp Gly Leu Pro Asn Leu Val Thr Asn Leu Ser Asp Pro Glu Cys
                180                 185                 190

Ala Gln Ala Asn Ser Ser Gly Ile Tyr Val Ala Ala Arg Tyr Ala
                195                 200                 205

Leu Asn Lys Leu His Ala Ile Gln Asn Val Tyr Thr Tyr Leu Asp Ile
                210                 215                 220

Ala His Ser Gly Trp Leu Gly Trp Asp Asn Asn Arg Gln Gly Ile Ile
225                 230                 235                 240

Thr Leu Tyr Thr Asp Val Val Ser Gly Thr Thr Ala Gly Leu Thr Ser
                245                 250                 255

Val Asp Gly Phe Val Thr Asn Thr Ala Asn Tyr Thr Pro Leu Val Glu
                260                 265                 270

Pro Asn Leu Val Asp Pro Ser Val Thr Val Gly Gly Gln Gln Leu Lys
                275                 280                 285

Ser Ala Lys Ile Tyr Glu Trp Asn Pro His Phe Asp Glu Thr Asp Phe
290                 295                 300

Thr Ala Ala Leu Tyr Thr Gly Phe Thr Ser Ala Gly Trp Pro Ala Ser
305                 310                 315                 320

Ile Gly Phe Leu Ile Asp Thr Ser Arg Asn Gly Trp Gly Gly Pro Asn
                325                 330                 335

Arg Pro Thr Gly Ala Val Gly Ser Thr Val Asp Ala Tyr Val Asp Ser
                340                 345                 350

Gly Arg Val Asp Arg Arg Ala His Arg Gly Leu Trp Cys Asn Gln Ser
                355                 360                 365

Gly Thr Gly Ile Gly Gln Ala Pro Gln Ser Ser Pro Ala Gly Tyr Thr
                370                 375                 380

Ala Ser Arg Leu Asp Ala Phe Val Trp Ile Lys Pro Pro Gly Glu Ser
385                 390                 395                 400

Asp Gly Ala Ser Lys Glu Ile Pro Asn Glu Glu Gly Lys Gly Ala Asp
```

```
            405                 410                 415
Pro Met Cys Asn Pro Asp Tyr Thr Thr Lys Tyr Asn Thr Lys Ala Gly
        420                 425                 430

Ala Leu Pro Asn Ala Pro Leu Ser Gly His Trp Phe His Asp Gln Phe
            435                 440                 445

Ala Met Leu Val Gln Asn Ala Tyr Pro Ala Ile Pro Pro Ala Gln Gly
        450                 455                 460

Asp Asn Glu Pro Pro Leu Ala Pro Thr Gly Leu Thr Ala Ser Pro Gly
465                 470                 475                 480

Asn Gln Gln Val Thr Leu Ser Trp Thr Ala Ser Pro Gly Ala Thr Ser
                485                 490                 495

Tyr Thr Val Lys Arg Gly Thr Ala Ser Thr Gly Pro Phe Ala Thr Val
            500                 505                 510

Thr Thr Val Thr Gly Thr Ala Tyr Thr His Thr Gly Leu Thr Asn Gly
        515                 520                 525

Thr Thr Tyr Tyr Phe Val Val Ser Ala Ser Asn Asn Asn Gly Ala Ser
        530                 535                 540

Ala His Thr Ser Ala Val Ser Ala Thr Pro Gly Asn Glu Ala Leu Ala
545                 550                 555                 560

Ala Pro Ala Gly Leu Leu Ala Thr Ala Gly Ser Ser Gln Ile Asn
                565                 570                 575

Leu Ser Trp Thr Gly Ser Ala Gly Ala Thr Gly Tyr Asn Ile Tyr Arg
            580                 585                 590

Ser Thr Ser Pro Asn Val Ala Met Thr Ala Ala Asn Arg Val Gly Asn
                595                 600                 605

Arg Ser Thr Thr Ser Phe Thr Asp Thr Gly Leu Thr Pro Asn Thr Ala
            610                 615                 620

Tyr Tyr Tyr Lys Val Thr Ala Phe Asn Ala Ser Leu Glu Ser Ala Ala
625                 630                 635                 640

Ser Asn Glu Ala Ser Ala Lys Thr Gln Asn Ile Ser Thr Gly Thr Leu
                645                 650                 655

Ser Ala Leu Tyr Arg Asp Gly Asp Asn Asn Ala Pro Gly Asn Asn Gln
            660                 665                 670

Ile Arg Pro His Leu Arg Val Lys Asn Gly Gly Thr Thr Pro Val Asn
            675                 680                 685

Leu Ala Glu Val Lys Val Arg Tyr
            690                 695

<210> SEQ ID NO 7
<211> LENGTH: 584
<212> TYPE: PRT
<213> ORGANISM: Paenibacillus sp. KSM-N145

<400> SEQUENCE: 7

Met Arg Ile His Ala Ile Arg Gln Ser Cys Arg Leu Val Leu Thr Met
1               5                   10                  15

Val Leu Met Leu Gly Leu Leu Pro Val Gly Ala Pro Lys Gly Tyr
            20                  25                  30

Ala Ala Pro Ala Val Pro Phe Gly Gln Leu Lys Val Gln Gly Asn Gln
        35                  40                  45

Leu Val Gly Gln Ser Gly Gln Ala Val Gln Leu Val Gly Met Ser Ser
    50                  55                  60

His Gly Leu Gln Trp Tyr Gly Asn Phe Val Asn Lys Ser Ser Leu Gln
65              70                  75                  80
```

```
Trp Met Arg Asp Asn Trp Gly Ile Asn Val Phe Arg Ala Ala Met Tyr
                85                  90                  95
Thr Ala Glu Asp Gly Tyr Ile Thr Asp Pro Ser Val Lys Asn Lys Val
            100                 105                 110
Lys Glu Ala Val Gln Ala Ser Ile Asp Leu Gly Leu Tyr Val Ile Ile
            115                 120                 125
Asp Trp His Ile Leu Ser Asp Gly Asn Pro Asn Thr Tyr Lys Ala Gln
            130                 135                 140
Ser Lys Ala Phe Phe Gln Glu Met Ala Thr Leu Tyr Gly Asn Thr Pro
145                 150                 155                 160
Asn Val Ile Tyr Glu Ile Ala Asn Glu Pro Asn Gly Asn Val Ser Trp
                165                 170                 175
Ala Asp Val Lys Ser Tyr Ala Glu Glu Val Ile Thr Ala Ile Arg Ala
            180                 185                 190
Ile Asp Pro Asp Gly Val Val Ile Val Gly Ser Pro Thr Trp Ser Gln
            195                 200                 205
Asp Ile His Leu Ala Ala Asp Asn Pro Val Ser His Ser Asn Val Met
            210                 215                 220
Tyr Ala Leu His Phe Tyr Ser Gly Thr His Gly Gln Phe Leu Arg Asp
225                 230                 235                 240
Arg Ile Thr Tyr Ala Met Asn Lys Gly Ala Ala Ile Phe Val Thr Glu
                245                 250                 255
Trp Gly Thr Ser Asp Ala Ser Gly Asn Gly Gly Pro Tyr Leu Pro Gln
            260                 265                 270
Ser Lys Glu Trp Ile Asp Phe Leu Asn Ala Arg Lys Ile Ser Trp Val
            275                 280                 285
Asn Trp Ser Leu Ala Asp Lys Val Glu Thr Ser Ala Ala Leu Met Pro
290                 295                 300
Gly Ala Ser Pro Thr Gly Gly Trp Thr Asp Ala Gln Leu Ser Glu Ser
305                 310                 315                 320
Gly Lys Trp Val Arg Asp Gln Ile Arg Gln Ala Thr Gly Gly Gly Ser
                325                 330                 335
Gly Asn Pro Thr Ala Pro Ala Ala Pro Thr Asn Leu Ser Ala Thr Ala
            340                 345                 350
Gly Asn Ala Gln Val Ser Leu Thr Trp Asn Ala Val Ser Gly Ala Thr
            355                 360                 365
Ser Tyr Thr Val Lys Arg Ala Thr Thr Ser Gly Gly Pro Tyr Thr Asn
            370                 375                 380
Val Ala Thr Gly Val Thr Ala Thr Ser Tyr Thr Asn Thr Gly Leu Thr
385                 390                 395                 400
Asn Gly Thr Thr Tyr Tyr Tyr Val Val Ser Ala Ser Asn Ser Ala Gly
                405                 410                 415
Ser Ser Ala Asn Ser Ala Gln Ala Ser Ala Thr Pro Ala Ser Gly Gly
            420                 425                 430
Ala Ser Thr Gly Asn Leu Val Val Gln Tyr Lys Val Gly Asp Thr Ser
            435                 440                 445
Ala Thr Asp Asn Gln Met Lys Pro Ser Phe Asn Ile Lys Asn Asn Gly
            450                 455                 460
Thr Thr Pro Val Asn Leu Ser Gly Leu Lys Leu Arg Tyr Tyr Phe Thr
465                 470                 475                 480
Lys Asp Gly Thr Ala Asp Met Ser Ala Ser Ile Asp Trp Ala Gln Ile
                485                 490                 495
Gly Ala Ser Asn Val Ser Ala Ala Phe Ala Asn Phe Thr Gly Ser Asn
```

-continued

```
                500                     505                     510
Thr Asp Thr Tyr Val Glu Leu Ser Phe Ser Ala Ala Ala Gly Ser Ile
        515                     520                     525

Pro Ala Gly Gly Gln Thr Gly Asp Ile Gln Leu Arg Met Tyr Lys Thr
        530                     535                     540

Asp Trp Ser Asn Phe Asn Glu Ala Asn Asp Tyr Ser Tyr Asp Gly Ala
545                     550                     555                     560

Lys Thr Ala Tyr Ala Asp Trp Asn Arg Val Thr Leu His Gln Asn Gly
                565                     570                     575

Thr Leu Val Trp Gly Thr Thr Pro
                580
```